(12) United States Patent
Roberts et al.

(10) Patent No.: US 7,405,204 B2
(45) Date of Patent: Jul. 29, 2008

(54) NUCLEOSIDE COMPOUNDS FOR TREATING VIRAL INFECTIONS

(75) Inventors: Christopher D. Roberts, Belmont, CA (US); Ronald Conrad Griffith, Escondido, CA (US); Natalia B. Dyatkina, Mountain View, CA (US); Marija Prhavc, Encinitas, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 108 days.

(21) Appl. No.: 11/411,434

(22) Filed: Apr. 25, 2006

(65) Prior Publication Data

US 2006/0241064 A1 Oct. 26, 2006

Related U.S. Application Data

(60) Provisional application No. 60/674,731, filed on Apr. 25, 2005.

(51) Int. Cl.
*A01N 43/04* (2006.01)
*A61K 31/70* (2006.01)
*C07H 19/00* (2006.01)
*C07H 19/04* (2006.01)

(52) U.S. Cl. .............................. 514/42; 514/43; 514/52; 536/22.1; 536/26.1; 536/27.1; 536/27.2

(58) Field of Classification Search .................. None
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 5,597,691 A | 1/1997 | Houghton et al. | |
| 5,607,915 A | 3/1997 | Patton | |
| 5,738,985 A | 4/1998 | Miles et al. | |
| 5,739,002 A | 4/1998 | De Francesco et al. | |
| 5,759,795 A | 6/1998 | Jubin et al. | |
| 5,861,267 A | 1/1999 | Su | |
| 6,030,785 A | 2/2000 | Katze et al. | |
| 6,228,576 B1 | 5/2001 | Delvecchio | |
| 6,479,651 B1 | 11/2002 | Seela et al. | |
| 7,094,768 B2 * | 8/2006 | Roberts et al. | 514/45 |
| 7,144,868 B2 * | 12/2006 | Roberts et al. | 514/43 |
| 7,151,089 B2 * | 12/2006 | Roberts et al. | 514/43 |
| 7,157,434 B2 * | 1/2007 | Keicher et al. | 514/43 |
| 7,169,918 B2 * | 1/2007 | Roberts et al. | 536/27.2 |
| 7,202,223 B2 * | 4/2007 | Roberts et al. | 514/43 |
| 7,244,713 B2 * | 7/2007 | Roberts et al. | 514/43 |
| 2006/0111311 A1 * | 5/2006 | Keicher et al. | 514/43 |
| 2006/0194749 A1 * | 8/2006 | Keicher et al. | 514/43 |

FOREIGN PATENT DOCUMENTS

| | | | |
|---|---|---|---|
| WO | WO 97/12033 A1 | 4/1997 | |
| WO | WO 02/057425 A | 7/2002 | |
| WO | WO 02/057425 A2 | 7/2002 | |
| WO | WO 2004/007512 A2 | 1/2004 | |
| WO | WO 2004/014313 A2 | 2/2004 | |
| WO | WO 2004/014852 A2 | 2/2004 | |
| WO | WO 2004/028481 A | 4/2004 | |
| WO | WO 2005/003147 A | 1/2005 | |
| WO | WO 2005/024268 A1 | 6/2005 | |

OTHER PUBLICATIONS

Wolff, Manfred E. "Burger's Medicinal Chemistry, 5ed, Part I", John Wiley & Sons, 1995, pp. 975-977.*

Banker, G.S. et al, "Modern Pharmaceutics, 3ed.", Marcel Dekker, New York, 1996, p. 596.*

Bartholomeusz, et al., "Hepatitis C Virus (HCV) RNA polymerase assay using cloned HCV non-structural proteins." Antiviral Therapy, 1996, 1 (supp. 4), 18-24.

Beaulieu, P.L. and Tsantrizos, Y. S., "Inhibitors of the HCV NS5B polymerase: new hope for the treatment of hepatitis C infections." Curr. Opin. Investig. Drugs 2004, 5, 838-50.

Conglatu, et al., "Novel Potential Anticancer Naphthyl Phosphoramidates of BVdU: Separation of Diastereoisomers and Assignment of the Absolute Configuration of the Phosphorous Center." J. Med. Chem., 2006, 49, 452-55.

Cooperwood, J. S., et al., "Nucleoside and Nucleotide prodrugs" in Ed(s) Chu, C. K. Recent Advances in Nucleosides (2002), 92-147.

Ferrari, et al., "Characterization of soluble hepatitis C virus RNA-dependent RNA polymerase expressed in *Escherichia coli*." J. Viro., 1999, 73, 1649-54.

Fried, et al., "Peginterferon alfa-2a plus ribavirin for chronic hepatitis C virus infection." N. Engl. J. Med., 2002, 347, 975-82.

Griffith, et al., "HCV Antiviral Agents." Ann. Rep. Med. Chem. 2004, 39, 223-37.

Gudmundsson, et al., "Phosphoramidate protides of carbocyclic 2',3'-dideoxy-2',3'-didehydro-7-deazaandenosine with potent activity against HIV and HBV." Nucleosides Nucleotides Nucleic Acids, 2004, 23(12), 1929-37..

Hoofnagle, "Hepatitis C: the clinical spectrum of disease." Hepatology 1997, 26, 15S-20S.

Horsmans, et al., "Isatoribine, an agonist of TLR7, reduces plasma virus concentration in chronic hepatitis C infection." Hepatology, 2005, 42, 724-31.

(Continued)

*Primary Examiner*—Shaojia Anna Jiang
*Assistant Examiner*—Traviss C McIntosh, III
(74) *Attorney, Agent, or Firm*—Foley & Lardner LLP; Junrui Yang

(57) ABSTRACT

Disclosed are compounds, compositions and methods for treating viral infections caused by a Flaviviridae family virus, such as hepatitis C virus.

48 Claims, No Drawings

OTHER PUBLICATIONS

Hutchinson, D.W. (Ed. Leroy B. Townsend) "The Synthesis, Reaction and Properties of Nucleoside Mono-, Di-, and Triphosphates, and Nucleosides with Changes in the Phosphoryl Residue" Chemistry of Nucleosides and Nucleotides, Plenum Press, 1991, 2.

Ishii, et al., "Expression of hepatitis C virus NS5B protein: characterization of its RNA polymerase activity and RNA binding," Hepatology, 1999, 29, 1227-35.

Lohmann, et al., "Replication of subgenomic hepatitis C virus RNAs in a hepatoma cell line." Science, 1999, 285, 110-13.

Lohmann, et al., "Selective Stimulation of Hepatitis C Virus and Pestivirus NS5B RNA Polymerase Activity by GTP." J. Bio. Chem., 1999, 274, 10807-15.

McGulgan, et al., "Anti-cancer ProTides: tuning the activity of BVDU phosphoramidates related to thymectacin." Bioorganic & Medicinal Chem. 2005, 13, 3219-27.

Meier, C., et al., Synlett 1998, 3, 233-42.

Moriishi and Matsuura, "Mechanisms of hepatitis C virus infection." Antivir. Chem. Chemother. 2003, 14, 285-97.

Ni, Z. J. and Wagman, A. S., "Progress and development of small molecule HCV antivirals." Curr. Opin. Drug Discov. Devel. 2004, 7, 446-59.

Prakash, et al., "Synthesis and evaluation of S-acyl-2-thioethyl esters of modified nucleoside 5'-monophosphates as inhibitors of hepatitis C virus RNA replication." J. Med. Chem., 2005, 48(4), 1199-1210.

Saunders and Raybuck, "Inosine Monophosphate Dehydrogenase: Consideration of Structure, Kinetics and Therapeutic Potential." Ann. Rep. Med. Chem., 2000, 35, 201-10.

Szabo, et al., "Viral hepatitis: new data on hepatitis C infection." Pathol. Oncol. Res. 2003, 9, 215-221.

Thomson and Finch, Clin Microbial Infect. 2005, 11, 86-94.

Wagner, C., et al., "Pronucleotides: Toward the in vivo delivery of antiviral and anticancer nucleotides." Medicinal Research Reviews 2000, 20(6), 417-451.

Watashi, et al., "Cytophilin B is a functional regulator of hepatitis C virus RNA polymerase." Molecular Cell, 2005, 19, 111-122.

Yamashita, et al., "RNA-dependent RNA Polymerase Activity of the Soluble Recombinant Hepatitis C Virus NS5B Protein Truncated at the C-terminal Region." J. Bio. Chem., 1998, 273, 15479-86.

Zemlicka, J., et al., "Lipophilic phosphoramidates as antiviral pronucleotides." Biochimica et Biophysica Acta (2002), 158(2-3), 276-286.

* cited by examiner

NUCLEOSIDE COMPOUNDS FOR TREATING VIRAL INFECTIONS

CROSS REFERENCE TO RELATED APPLICATION

This application claims the benefit under 35 U.S.C. 119(e) to provisional applications U.S. Ser. No. 60/674,731 filed on Apr. 25, 2005 which is incorporated herein by reference in its entirety.

BACKGROUND OF THE INVENTION

Field of the Invention

The invention relates to methods for preparing-particular compounds for treating viral infections in mammals mediated, at least in part, by a virus in the Flaviviridae family of viruses. This invention is also directed to novel intermediates utilized in these methods.

REFERENCES

The following publications are cited in this application as superscript numbers:
1. Szabo, et al., *Pathol.Oncol.Res.* 2003, 9:215-221.
2. Hoofnagle J H, *Hepatology* 1997, 26:15S-20S.
3. Thomson B J and Finch R G, *Clin Microbial Infect.* 2005, 11:86-94.
4. Moriishi K and Matsuura Y, *Antivir.Chem.Chemother.* 2003, 14:285-297.
5. Fried, et al. *N. Engl. J Med* 2002, 347:975-982.
6. Ni, Z. J. and Wagman, A. S. *Curr. Opin. Drug Discov. Devel.* 2004, 7, 446-459.
7. Beaulieu, P. L. and Tsantrizos, Y. S. *Curr. Opin. Investig. Drugs* 2004, 5, 838-850.
8. Griffith, et al., *Ann. Rep. Med. Chem* 39, 223-237, 2004.
9. Watashi, et al, Molecular Cell, 19, 111-122, 2005
10. Horsmans, et al., Hepatology, 42, 724-731, 2005

STATE OF THE ART

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load[5] and there is a clear need for more effective antiviral therapy of HCV infection.

A number of approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.[6-8]

Besides targeting viral genes and their transcription and translation products, antiviral activity can also be achieved by targeting host cell proteins that are necessary for viral replication. For example, Watashi et al[9] show how antiviral activity can be achieved by inhibiting host cell cyclophilins. Alternatively, a potent TLR7 agonist has been shown to reduce HCV plasma levels in humans.[10]

However, none of the compounds described above have progressed beyond clinical trials.[6,8]

In view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

This invention is directed to novel compounds that are useful in the treatment of viral infections in mammals mediated, at least in part, by a virus in the Flaviviridae family of viruses. Specifically, this invention is directed to compounds of formula I as follows:

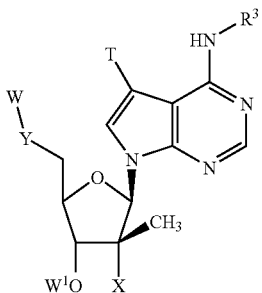

wherein:
Y is O or $CH_2$;
X is selected from halo and $O-W^2$;
each of W, $W^1$ and $W^2$ is independently selected from the group consisting of hydrogen, $C_1$-$C_4$ alkyl, and a pharmaceutically acceptable prodrug group, provided that when X is $-O-W^2$, one of W, $W^1$ and $W^2$ is $C_1$-$C_4$ alkyl;
$R^3$ is selected from the group consisting of hydrogen, OH, acyl, $C_1$-$C_4$ alkyl, and $C_1$-$C_4$ alkoxy;
T is selected from the group consisting of:
a) $-C\equiv C-R$, where R is selected from the group consisting of:
  i) hydrogen;
  ii) tri($C_1$-$C_4$)alkylsilyl, $-C(O)NR^1R^2$, alkoxyalkyl, heteroaryl, substituted heteroaryl, phenyl, and substituted phenyl;
  where $R^1$ and $R^2$ are independently selected from the group consisting of hydrogen, alkyl, substituted alkyl, amino, substituted amino, aryl, substituted aryl, heteroaryl, substituted heteroaryl, heterocyclic and substituted heterocyclic provided that only one of $R^1$ and $R^2$ is amino or substituted amino, and further wherein $R^1$ and $R^2$, together with the nitrogen atom pendant thereto, form a heterocyclic or substituted heterocyclic; and
  iii) $-C(O)OR^{14}$, where $R^{14}$ is selected from the group consisting of hydrogen, alkyl or substituted alkyl;
b) $-CH=CH-Q^2$, where $Q^2$ is selected from hydrogen or cis-alkoxy;
c) $-C(O)H$;
d) $-CH=NNHR^{15}$, where $R^{15}$ is hydrogen or $C_1$-$C_4$ alkyl;
e) $-CH=N(OR^{15})$, where $R^{15}$ is as defined above;
f) $-CH(OR^{16})_2$, where $R^{16}$ is $C_3$-$C_6$ alkyl;
g) $-B(OR^{15})_2$, where $R^{15}$ is as defined above; and
h) $-NO_2$;
or pharmaceutically acceptable salts or partial salts thereof;

provided that when $R^3$ is hydrogen, OH, or $C_1$-$C_3$ alkoxy, then X is halo or $-O(C_1$-$C_4$ alkyl).

In one embodiment, Y is O and W is hydrogen and $W^1$ is hydrogen. In some aspects, X is halo.

In another embodiment, $R^3$ is hydrogen. In some aspects, X is halo.

In one embodiment, T is $-C\equiv C-R$ and R is hydrogen. In some aspects, X is halo.

In another embodiment T is $-C\equiv C-R$ and R is selected from the group consisting of tri($C_1$-$C_4$)alkylsilyl, $-C(O)NR_1R^2$, alkoxyalkyl, heteroaryl, substituted heteroaryl, phenyl, and substituted phenyl. In a preferred embodiment, R is selected from the group consisting of phenyl, $-C(O)NH_2$, $-Si(CH_3)_3$, pyrid-2-yl, 4-methoxyphenyl, and $-CH(OCH_2CH_3)_2$. In some aspects, X is halo.

In another embodiment, T is $-C\equiv C-R$ and R is $-C(O)$OH. In some aspects, X is halo.

In another embodiment, T is $-C\equiv C-R$, R is $-C(O)OR^{14}$, and $R^{14}$ is alkyl. In some aspects, X is halo.

In another embodiment, T is $-CH=CH-Q^2$, where $Q^2$ is selected from hydrogen or cis-methoxy. In some aspects, X is halo.

In another embodiment, T is $-C(=O)H$. In some aspects, X is halo.

In another embodiment, T is $-CH=NNHR^{15}$. In some aspects, X is halo.

In another embodiment, T is $-CH=N(OR^{15})$. In some aspects, X is halo.

In another embodiment, T is $-CH(OR^{16})_2$. In some aspects, X is halo.

In another embodiment, T is $-B(OR^{15})_2$. In some aspects, X is halo.

In another embodiment, T is $-NO_2$. In some aspects, X is halo.

In one embodiment, X is halo, preferably fluoro.

In another embodiment, X is $O-W^2$, and $W^2$ is $C_1$-$C_4$ alkyl, preferably methyl.

In another embodiment, T is $-C\equiv C-H$, X is F, and Y is O.

In another embodiment, the compounds of this invention are represented by formula Ia as follows:

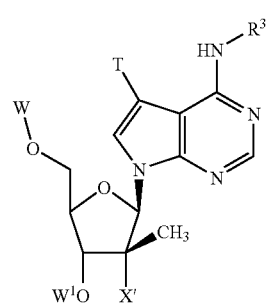

wherein:
X' is $-OW^2$ and $W^2$ is $C_1$-$C_4$ alkyl;
each of W and $W^1$ is independently hydrogen or a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and $-C(O)CHR^{30}NHR^{31}$ where $R^{30}$ is selected from the group consisting of hydrogen, alkyl, substituted alkyl, aryl, substituted aryl, heteroaryl and substituted heteroaryl and $R^{31}$ is hydrogen or $R^{30}$ together with the carbon atom pendent thereto and $R^{31}$ together with the nitrogen atom pendent thereto join to form a heterocyclic or substituted heterocyclic ring;
$R^3$ is selected from the group consisting of hydrogen, OH, acyl, $C_1$-$C_4$ alkyl, and $C_1$-$C_4$ alkoxy;
T is selected from the group consisting of:
a) $-C\equiv C-R$, where R is selected from the group consisting of i) hydrogen;
ii) tri($C_1$-$C_4$)alkylsilyl, —C(O)NR$_1$R$^2$, alkoxyalkyl, heteroaryl, substituted heteroaryl, phenyl, and substituted phenyl;
where R$^1$ and R$^2$ are independently selected from the group consisting of hydrogen, alkyl, substituted alkyl, amino, substituted amino, aryl, substituted aryl, heteroaryl, substituted heteroaryl, heterocyclic and substituted heterocyclic provided that only one of R$^1$ and R$^2$ is amino or substituted amino, and further wherein R$^1$ and R$^2$, together with the nitrogen atom pendant thereto, form a heterocyclic or substituted heterocyclic; and
iii) —C(O)OR$^{14}$, where R$^{14}$ is hydrogen, alkyl or substituted alkyl;
b) —CH=CH-Q$^2$, where Q$^2$ is selected from hydrogen or cis-alkoxy;
c) —C(O)H;
d) —CH=NNHR$^{15}$, where R$^{15}$ is hydrogen or $C_1$-$C_4$ alkyl;
e) —CH=N(OR$^{15}$), where R$^{15}$ is as defined above;
f) —CH(OR$^{16}$)$_2$, where R$^{16}$ is $C_3$-$C_6$ alkyl;
g) —B(OR$^{15}$)$_2$, where R$^{15}$ is as defined above; and
h) —NO$_2$;
or a pharmaceutically acceptable salt thereof.

In another embodiment, R$^3$ is hydrogen.

In one preferred embodiment of formula Ia, W$^2$ is methyl and at least one of W or W$^1$ is hydrogen. More preferably, both W and W$^1$ are H.

In another preferred embodiment, W$^2$ is methyl, W is hydrogen, and W$^1$ is a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$. Preferably, R$^{30}$ (and optionally together with R$^{31}$) is a sidechain of an amino acid and more preferably is derived from an L-amino acid.

In another preferred embodiment, W$^2$ is methyl, and W$^1$ is hydrogen, and W is a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$.

In another embodiment, the compounds of this invention are represented by formula Ib as follows:

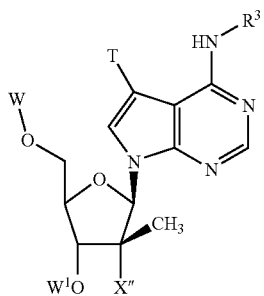

Ib wherein:
X" is halo;
each of W and W', is independently hydrogen or a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$ where R$^{30}$ is selected from the group consisting of hydrogen, alkyl, substituted alkyl, aryl, substituted aryl, heteroaryl and substituted heteroaryl and R$^{31}$ is hydrogen or R$^{30}$ together with the carbon atom pendent thereto and R$^{31}$ together with the nitrogen atom pendent thereto join to form a heterocyclic or substituted heterocyclic ring;
R$^3$ is selected from the group consisting of hydrogen, OH, acyl, $C_1$-$C_4$ alkyl, and $C_1$-$C_4$ alkoxy;
T is selected from the group consisting of:
a) —C≡C—R, where R is selected from the group consisting of
i) hydrogen;
ii) tri($C_1$-$C_4$)alkylsilyl, —C(O)NR$_1$R$^2$, alkoxyalkyl, heteroaryl, substituted heteroaryl, phenyl, and substituted phenyl;
where R$^1$ and R$^2$ are independently selected from the group consisting of hydrogen, alkyl, substituted alkyl, amino, substituted amino, aryl, substituted aryl, heteroaryl, substituted heteroaryl, heterocyclic and substituted heterocyclic provided that only one of R$^1$ and R$^2$ is amino or substituted amino, and further wherein R$^1$ and R$^2$, together with the nitrogen atom pendant thereto, form a heterocyclic or substituted heterocyclic;
iii) —C(O)OR$^{14}$, where R$^{14}$ is hydrogen, alkyl or substituted alkyl;
b) —CH=CH-Q$^2$, where Q$^2$ is selected from hydrogen or cis-alkoxy;
c) —C(O)H;
d) —CH=NNHR$^{15}$, where R$^{15}$ is hydrogen or $C_1$-$C_4$ alkyl;
e) —CH=N(OR$^{15}$), where R$^{15}$ is as defined above;
f) —CH(OR$^{16}$)$_2$, where R$^{16}$ is $C_3$-$C_6$ alkyl;
g) —B(OR$^{15}$)$_2$, where R$^{15}$ is as defined above; and
h) —NO$_2$;
or pharmaceutically acceptable salts thereof.

In one embodiment, R$^3$ is hydrogen.

In another embodiment, T is —C≡C—H, X is F, and Y is O.

In one preferred embodiment, X is fluoro, and at least one of W or W$^1$ is hydrogen. More preferably, both W and W$^1$ are hydrogen.

In another preferred embodiment, X is fluoro, W$^1$ is hydrogen, and W is a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$. Preferably, R$^{30}$ (and optionally together with R$^{31}$) is a sidechain of an amino acid and more preferably is derived from an L-amino acid.

In still another preferred embodiment, X is fluoro, W is hydrogen, and W$^1$ is a pharmaceutically acceptable prodrug selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$. Preferably, R$^{30}$ (and optionally together with R$^{31}$) is a sidechain of an amino acid and more preferably is derived from an L-amino acid.

In still another preferred embodiment X is O—W² where W² is C₁-C₄ alkyl, preferably methyl, one of W and W¹ is hydrogen, and the other of W and W¹ is represented by the formula:

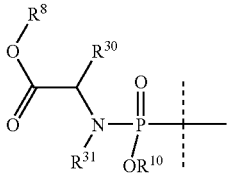

where R³⁰ and R³¹ are as defined above, R⁸ is hydrogen or alkyl and R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic. In a preferred embodiment R³⁰ (and optionally together with R³¹) is derived from an L-amino acid.

In still another preferred embodiment X is halo, more preferably fluoro, one of W and W¹ is hydrogen, and the other of W and W¹ is represented by the formula:

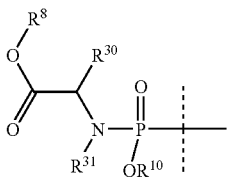

where R³⁰ and R³¹ as defined above, R⁸ is hydrogen or alkyl and R¹⁰ is selected from the group consisting of alkyl, substituted alkyl, aryl, substituted aryl, cycloalkyl, substituted cycloalkyl, heteroaryl, substituted heteroaryl, heterocyclic and substituted heterocyclic. In a preferred embodiment R³⁰ (and optionally together with R³¹) is derived from an L-amino acid.

In still another preferred embodiment X is O—W² where W² is C₁-C₄ alkyl, preferably methyl, one of W and W¹ is hydrogen, and the other of W and W¹ is represented by the formula:

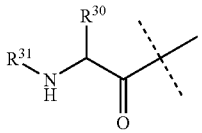

where R³⁰ and R³¹ are as defined above. As before, R³⁰ (and optionally together with R³¹) is preferably derived from an L amino acid.

In still another preferred embodiment X is halo, more preferably fluoro, one of W and W¹ is hydrogen, and the other of W and W¹ is represented by the formula:

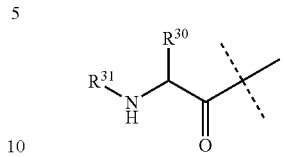

where R³⁰ and R³¹ are as defined above. As before, R³⁰ is preferably derived from an L amino acid.

In another embodiment one of W or W¹ is a bis-SATE(S-acyl-2-thioethyl)phosponate prodrug group where R is an alkyl group:

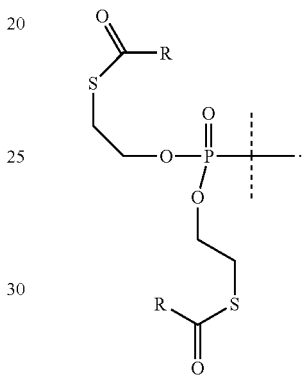

In other embodiments, W is a bis-SATE (S-acyl-2-thioethyl)phosphonate prodrug group.

Compounds of this invention are either active as antiviral agents or are useful as intermediates in the preparation of antiviral agents as described herein.

This invention is also directed to pharmaceutical compositions comprising a pharmaceutically acceptable diluent and a therapeutically effective amount of a compound as described herein or mixtures of one or more of such compounds.

This invention is still further directed to methods for treating a viral infection mediated, at least in part, by a virus in the Flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of a compound as described herein or mixtures of one or more of such compounds.

In yet another embodiment of the invention, methods of treating or preventing viral infections in mammals are provided wherein the compounds of this invention are administered in combination with the administration of a therapeutically effective amount of one or more agents active against HCV. Active agents against HCV include ribavirin, levovirin, viramidine, thymosin alpha-1, an inhibitor of NS3/4A serine protease, and inhibitor of inosine monophosphate dehydrogenase, interferon-alpha, pegylated interferon-alpha, alone or in combination with viramidine, ribavirin or levovirin. Preferably the additional agent active against HCV is interferon-alpha or pegylated interferon-alpha alone or in combination with viramidine, ribavirin or levovirin.

This invention is also directed to uses of the compounds as described herein or mixtures of one or more of such compounds in the preparation of a medicament for treating a viral infection mediated, at least in part, by a virus in the Flaviviridae family of viruses, such as HCV. Such compounds may also be used in combination with a therapeutically effective amount of one or more agents active against HCV as described herein.

Compounds of this invention include those set forth in Table I below and the mono, di, or tri-phosphates thereof:

TABLE I

| Compound | Name |
|---|---|
|  | 7-(2'-deoxy-2'-fluoro-2'-C-methyl-β-D-ribofuranosyl)-4-amino-5-nitro-pyrrolo[2,3-d]pyrimidine |
|  | 7-(2'-deoxy-2'-fluoro-2'-C-methyl-β-D-ribofuranosyl)-4-amino-5-(phenylacetylenyl)-pyrrolo[2,3-d]pyrimidine |
|  | 7-(2'-deoxy-2'-fluoro-2'-C-methyl-β-D-ribofuranosyl)-4-amino-5-formyl-pyrrolo[2,3-d]pyrimidine |
|  | 7-(2'-deoxy-2'-fluoro-2'-C-methyl-β-D-ribofuranosyl)-4-amino-5-boronic acid-pyrrolo[2,3-d]pyrimidine |

TABLE I-continued

| Compound | Name |
|---|---|
| (structure) | 4-Amino-5-ethynyl-7-(2-deoxy-2-fluoro-2-C-methyl-β-D-ribofuanosyl)-7H-pyrrolo[2,3-d]pyrimidine |
| (structure) | 7-(2'-deoxy-2'-fluoro-2'-C-methyl-β-D-ribofuranosyl)-4-amino-5-(trimethylsilylacetylenyl)-pyrrolo[2,3-d]pyrimidine |
| (structure) | 7-(2'-deoxy-2'-fluoro-2'-C-methyl-β-D-ribofuranosyl)-4-amino-5-ethenyl-pyrrolo[2,3-d]pyrimidine |
| (structure) | 7-(2'-deoxy-2'-fluoro-2'-C-methyl-β-D-ribofuranosyl)-4-amino-5-methylenehydrazine-pyrrolo[2,3-d]pyrimidine |
| (structure) | 7-(2'-deoxy-2'-fluoro-2'-C-methyl-β-D-ribofuranosyl)-4-amino-5-(carbaldehyde-oxime)-pyrrolo[2,3-d]pyrimidine(cis/trans or a mixture thereof) |

TABLE I-continued

| Compound | Name |
|---|---|
| (structure) | 7-(2'-deoxy-2'-fluoro-2'-C-methyl-β-D-ribo-furanosyl)-4-hydroxyamino-5-nitro-pyrrolo[2,3-d]pyrimidine |
| (structure) | 7-(2'-deoxy-2'-fluoro-2'-C-methyl-β-D-ribo-furanosyl)-4-hydroxyamino-5-(phenyl-acetylenyl)-pyrrolo[2,3-d]py-rimidine |
| (structure) | 7-(2'-deoxy-2'-fluoro-2'-C-methyl-β-D-ribo-furanosyl)-4-hydroxyamino-5-formyl-pyrrolo[2,3-d]pyrimidine |
| (structure) | 7-(2'-deoxy-2'-fluoro-2'-C-methyl-β-D-ribo-furanosyl)-4-hydroxyamino-5-boronic acid-pyrrolo[2,3-d]pyrimidine |

TABLE I-continued

| Compound | Name |
|---|---|
| | 7-(2'-deoxy-2'-fluoro-2'-C-methyl-β-D-ribofuranosyl)-4-hydroxyamino-5-acetylenyl-pyrrolo[2,3-d]pyrimidine |
| | 7-(2'-deoxy-2'-fluoro-2'-C-methyl-β-D-ribofuranosyl)-4-hydroxyamino-5-(trimethylsilylacetylenyl)-pyrrolo[2,3-d]pyrimidine |
| | 7-(2'-deoxy-2'-fluoro-2'-C-methyl-β-D-ribofuranosyl)-4-hydroxyamino-5-ethenyl-pyrrolo[2,3-d]pyrimidine |
| | 7-(2'-deoxy-2'-fluoro-2'-C-methyl-β-D-ribofuranosyl)-4-hydroxyamino-5-methylenehydrazine-pyrrolo[2,3-d]pyrimidine |
| | 7-(2'-deoxy-2'-fluoro-2'-C-methyl-β-D-ribofuranosyl)-4-hydroxyamino-5-(carbaldehyde-oxime)-pyrrolo[2,3-d]pyrimidine(cis/trans or a mixture thereof) |

TABLE I-continued

| Compound | Name |
|---|---|
| | 7-(2'-deoxy-2'-fluoro-2'-C-methyl-β-D-ribo-furanosyl)-4-acetylamino-5-nitro-pyrrolo[2,3-d]pyrimidine |
| | 7-(2'-deoxy-2'-fluoro-2'-C-methyl-β-D-ribo-furanosyl)-4-acetylamino-5-(phenyl-acetylenyl)-pyrrolo[2,3-d]pyrimidine |
| | 7-(2'-deoxy-2'-fluoro-2'-C-methyl-β-D-ribo-furanosyl)-4-acetylamino-5-formyl-pyrrolo[2,3-d]pyrimidine |
| | 7-(2'-deoxy-2'-fluoro-2'-C-methyl-β-D-ribo-furanosyl)-4-acetylamino-5-boronic acid-pyrrolo[2,3-d]pyrimidine |

TABLE I-continued

| Compound | Name |
|---|---|
| | 7-(2'-deoxy-2'-fluoro-2'-C-methyl-β-D-ribo-furanosyl)-4-acetylamino-5-acetyl-enyl-pyrrolo[2,3-d]pyrimidine |
| | 7-(2'-deoxy-2'-fluoro-2'-C-methyl-β-D-ribo-furanosyl)-4-acetylamino-5-(tri-methylsilylacetylenyl)-pyrrolo[2,3-d]pyrimidine |
| | 7-(2'-deoxy-2'-fluoro-2'-C-methyl-β-D-ribo-furanosyl)-4-acetylamino-5-ethenyl-pyrrolo[2,3-d]pyrimidine |
| | 7-(2'-deoxy-2'-fluoro-2'-C-methyl-β-D-ribo-furanosyl)-4-acetylamino-5-methylenehydrazine-pyrrolo[2,3-d]pyrimidine |

TABLE I-continued

| Compound | Name |
|---|---|
| 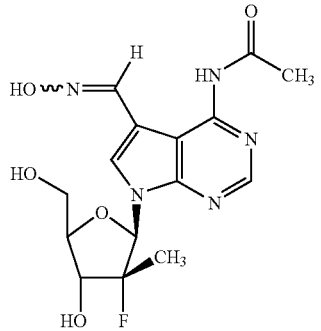 | 7-(2'-deoxy-2'-fluoro-2'-C-methyl-β-D-ribo-furanosyl)-4-acetylamino-5-(carb-aldehyde-oxime)-pyrrolo[2,3-d]py-rimidine(cis/ trans or a mixture thereof) |
| 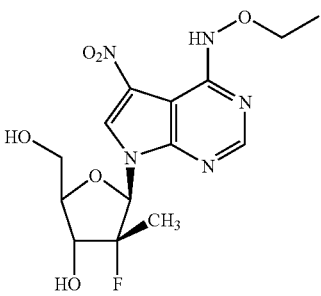 | 7-(2'-deoxy-2'-fluoro-2'-C-methyl-β-D-ribo-furanosyl)-4-ethoxyamino-5-nitro-pyrrolo[2,3-d]pyrimidine |
| 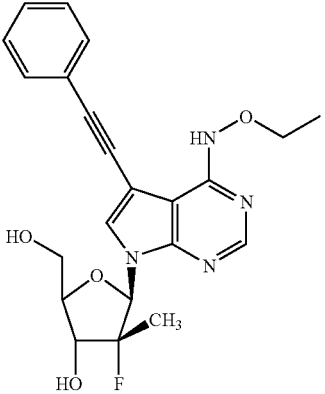 | 7-(2'-deoxy-2'-fluoro-2'-C-methyl-β-D-ribo-furanosyl)-4-ethoxyamino-5-(phenyl-acetylenyl)-pyrrolo[2,3-d]py-rimidine |
| 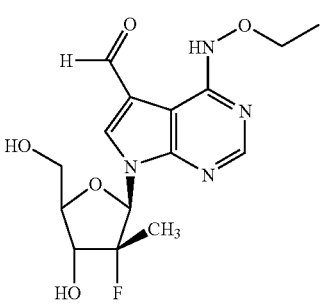 | 7-(2'-deoxy-2'-fluoro-2'-C-methyl-β-D-ribo-furanosyl)-4-ethoxyamino-5-formyl-pyrrolo[2,3-d]pyrimidine |

TABLE I-continued

| Compound | Name |
|---|---|
| (structure) | 7-(2'-deoxy-2'-fluoro-2'-C-methyl-β-D-ribo-furanosyl)-4-ethoxyamino-5-boronic acid-pyrrolo[2,3-d]pyrimidine |
| (structure) | 7-(2'-deoxy-2'-fluoro-2'-C-methyl-β-D-ribo-furanosyl)-4-ethoxyamino-5-acetyl-enyl-pyrrolo[2,3-d]pyrimidine |
| (structure) | 7-(2'-deoxy-2'-fluoro-2'-C-methyl-β-D-ribo-furanosyl)-4-ethoxyamino-5-(tri-methylsilylacetylenyl)-pyrrolo[2,3-d]pyrimidine |
| (structure) | 7-(2'-deoxy-2'-fluoro-2'-C-methyl-β-D-ribo-furanosyl)-4-ethoxyamino-5-ethenyl-pyrrolo[2,3-d]pyrimidine |
| (structure) | 7-(2'-deoxy-2'-fluoro-2'-C-methyl-β-D-ribo-furanosyl)-4-ethoxyamino-5-methyl-enehydrazine-pyrrolo[2,3-d]pyrimidine |

TABLE I-continued

| Compound | Name |
|---|---|
| | 7-(2'-deoxy-2'-fluoro-2'-C-methyl-β-D-ribo-furanosyl)-4-ethoxyamino-5-(carb-aldehyde-oxime)-pyrrolo[2,3-d]pyrimidine(cis/trans or a mixture thereof) |
| | 7-(2'-deoxy-2'-chloro-2'-C-methyl-β-D-ribo-furanosyl)-4-amino-5-nitro-pyrrolo[2,3-d]pyrimidine |
| | 7-(2'-deoxy-2'-chloro-2'-C-methyl-β-D-ribo-furanosyl)-4-amino-5-(phenyl-acetylenyl)-pyrrolo[2,3-d]pyrimidine |
| | 7-(2'-deoxy-2'-chloro-2'-C-methyl-β-D-ribo-furanosyl)-4-amino-5-formyl-pyrrolo[2,3-d]pyrimidine |
| | 7-(2'-deoxy-2'-chloro-2'-C-methyl-β-D-ribo-furanosyl)-4-amino-5-boronic acid-pyrrolo[2,3-d]pyrimidine |

TABLE I-continued

| Compound | Name |
|---|---|
| | 7-(2'-deoxy-2'-chloro-2'-C-methyl-β-D-ribofuranosyl)-4-amino-5-acetylenyl-pyrrolo[2,3-d]pyrimidine |
| | 7-(2'-deoxy-2'-chloro-2'-C-methyl-β-D-ribofuranosyl)-4-amino-5-(trimethylsilylacetylenyl)-pyrrolo[2,3-d]pyrimidine |
| | 7-(2'-deoxy-2'-chloro-2'-C-methyl-β-D-ribofuranosyl)-4-amino-5-ethenyl-pyrrolo[2,3-d]pyrimidine |
| | 7-(2'-deoxy-2'-chloro-2'-C-methyl-β-D-ribofuranosyl)-4-amino-5-methylenehydrazine-pyrrolo[2,3-d]pyrimidine |
| | 7-(2'-deoxy-2'-chloro-2'-C-methyl-β-D-ribofuranosyl)-4-amino-5-(carbaldehyde-oxime)-pyrrolo[2,3-d]pyrimidine(cis/trans or a mixture thereof) |

TABLE I-continued

| Compound | Name |
|---|---|
| | 7-(2'-deoxy-2'-chloro-2'-C-methyl-β-D-ribo-furanosyl)-4-hydroxyamino-5-nitro-pyrrolo[2,3-d]pyrimidine |
| | 7-(2'-deoxy-2'-chloro-2'-C-methyl-β-D-ribo-furanosyl)-4-hydroxyamino-5-(phenyl-acetylenyl)-pyrrolo[2,3-d]pyrimidine |
| | 7-(2'-deoxy-2'-chloro-2'-C-methyl-β-D-ribo-furanosyl)-4-hydroxyamino-5-formyl-pyrrolo[2,3-d]pyrimidine |
| | 7-(2'-deoxy-2'-chloro-2'-C-methyl-β-D-ribo-furanosyl)-4-hydroxyamino-5-boronic acid-pyrrolo[2,3-d]pyrimidine |

TABLE I-continued

| Compound | Name |
|---|---|
| (structure) | 7-(2'-deoxy-2'-chloro-2'-C-methyl-β-D-ribofuranosyl)-4-hydroxyamino-5-acetylenyl-pyrrolo[2,3-d]pyrimidine |
| (structure) | 7-(2'-deoxy-2'-chloro-2'-C-methyl-β-D-ribofuranosyl)-4-hydroxyamino-5-(trimethylsilylacetylenyl)-pyrrolo[2,3-d]pyrimidine |
| (structure) | 7-(2'-deoxy-2'-chloro-2'-C-methyl-β-D-ribofuranosyl)-4-hydroxyamino-5-ethenyl-pyrrolo[2,3-d]pyrimidine |
| (structure) | 7-(2'-deoxy-2'-chloro-2'-C-methyl-β-D-ribofuranosyl)-4-hydroxyamino-5-methylenehydrazine-pyrrolo[2,3-d]pyrimidine |
| (structure) | 7-(2'-deoxy-2'-chloro-2'-C-methyl-β-D-ribofuranosyl)-4-hydroxyamino-5-(carbaldehyde-oxime)-pyrrolo[2,3-d]pyrimidine(cis/trans or a mixture thereof) |

TABLE I-continued

| Compound | Name |
|---|---|
| | 7-(2'-deoxy-2'-chloro-2'-C-methyl-β-D-ribo-furanosyl)-4-acetylamino-5-nitro-pyrrolo[2,3-d]pyrimidine |
| | 7-(2'-deoxy-2'-chloro-2'-C-methyl-β-D-ribo-furanosyl)-4-acetylamino-5-(phenyl-acetylenyl)-pyrrolo[2,3-d]pyrimidine |
| | 7-(2'-deoxy-2'-chloro-2'-C-methyl-β-D-ribo-furanosyl)-4-acetylamino-5-formyl-pyrrolo[2,3-d]pyrimidine |
| | 7-(2'-deoxy-2'-chloro-2'-C-methyl-β-D-ribo-furanosyl)-4-acetylamino-5-boronic acid-pyrrolo[2,3-d]pyrimidine |

TABLE I-continued

| Compound | Name |
|---|---|
| (structure) | 7-(2'-deoxy-2'-chloro-2'-C-methyl-β-D-ribo-furanosyl)-4-acetylamino-5-acetyl-enyl-pyrrolo[2,3-d]pyrimidine |
| (structure) | 7-(2'-deoxy-2'-chloro-2'-C-methyl-β-D-ribo-furanosyl)-4-acetylamino-5-(tri-methylsilylacetylenyl)-pyrrolo[2,3-d]pyrimidine |
| (structure) | 7-(2'-deoxy-2'-chloro-2'-C-methyl-β-D-ribo-furanosyl)-4-acetylamino-5-ethenyl-pyrrolo[2,3-d]pyrimidine |
| (structure) | 7-(2'-deoxy-2'-chloro-2'-C-methyl-β-D-ribo-furanosyl)-4-acetylamino-5-methylenehydrazine-pyrrolo[2,3-d]pyrimidine |

TABLE I-continued

| Compound | Name |
|---|---|
| | 7-(2'-deoxy-2'-chloro-2'-C-methyl-β-D-ribo-furanosyl)-4-acetylamino-5-(carb-aldehyde-oxime)-pyrrolo[2,3-d]pyrimidine(cis/trans or a mixture thereof) |
| | 7-(2'-deoxy-2'-chloro-2'-C-methyl-β-D-ribo-furanosyl)-4-ethoxyamino-5-nitro-pyrrolo[2,3-d]pyrimidine |
| | 7-(2'-deoxy-2'-chloro-2'-C-methyl-β-D-ribo-furanosyl)-4-ethoxyamino-5-(phenyl-acetylenyl)-pyrrolo[2,3-d]pyrimidine |
| | 7-(2'-deoxy-2'-chloro-2'-C-methyl-β-D-ribo-furanosyl)-4-ethoxyamino-5-formyl-pyrrolo[2,3-d]pyrimidine |

TABLE I-continued

| Compound | Name |
|---|---|
| | 7-(2'-deoxy-2'-chloro-2'-C-methyl-β-D-ribo-furanosyl)-4-ethoxyamino-5-boronic acid-pyrrolo[2,3-d]pyrimidine |
| | 7-(2'-deoxy-2'-chloro-2'-C-methyl-β-D-ribo-furanosyl)-4-ethoxyamino-5-acetyl-enyl-pyrrolo[2,3-d]pyrimidine |
| | 7-(2'-deoxy-2'-chloro-2'-C-methyl-β-D-ribo-furanosyl)-4-ethoxyamino-5-(tri-methylsilylacetylenyl)-pyrrolo[2,3-d]pyrimidine |
| | 7-(2'-deoxy-2'-chloro-2'-C-methyl-β-D-ribo-furanosyl)-4-ethoxyamino-5-ethenyl-pyrrolo[2,3-d]pyrimidine |
| | 7-(2'-deoxy-2'-chloro-2'-C-methyl-β-D-ribo-furanosyl)-4-ethoxyamino-5-methylenehydrazine-pyrrolo[2,3-d]pyrimidine |

TABLE I-continued

| Compound | Name |
|---|---|
| | 7-(2'-deoxy-2'-chloro-2'-C-methyl-β-D-ribo-furanosyl)-4-ethoxyamino-5-(carb-aldehyde-oxime)-pyrrolo[2,3-d]pyrimidine(cis/trans or a mixture thereof) |
| | 7-(2'-deoxy-2'-bromo-2'-C-methyl-β-D-ribo-furanosyl)-4-amino-5-nitro-pyrrolo[2,3-d]pyrimidine |
| | 7-(2'-deoxy-2'-bromo-2'-C-methyl-β-D-ribo-furanosyl)-4-amino-5-(phenyl-acetylenyl)-pyrrolo[2,3-d]pyrimidine |
| | 7-(2'-deoxy-2'-bromo-2'-C-methyl-β-D-ribo-furanosyl)-4-amino-5-formyl-pyrrolo[2,3-d]pyrimidine |
| | 7-(2'-deoxy-2'-bromo-2'-C-methyl-β-D-ribo-furanosyl)-4-amino-5-boronic acid-pyrrolo[2,3-d]pyrimidine |

TABLE I-continued

| Compound | Name |
|---|---|
| (structure) | 7-(2'-deoxy-2'-bromo-2'-C-methyl-β-D-ribo-furanosyl)-4-amino-5-acetylenyl-pyrrolo[2,3-d]pyrimidine |
| (structure) | 7-(2'-deoxy-2'-bromo-2'-C-methyl-β-D-ribo-furanosyl)-4-amino-5-(tri-methylsilylacetylenyl)-pyrrolo[2,3-d]pyrimidine |
| (structure) | 7-(2'-deoxy-2'-bromo-2'-C-methyl-β-D-ribo-furanosyl)-4-amino-5-ethenyl-pyrrolo[2,3-d]pyrimidine |
| (structure) | 7-(2'-deoxy-2'-bromo-2'-C-methyl-β-D-ribo-furanosyl)-4-amino-5-methylhydrazine-pyrrolo[2,3-d]pyrimidine |
| (structure) | 7-(2'-deoxy-2'-bromo-2'-C-methyl-β-D-ribo-furanosyl)-4-amino-5-(carbaldehyde-oxime)-pyrrolo[2,3-d]pyrimidine(cis/trans or a mixture thereof) |

TABLE I-continued

| Compound | Name |
|---|---|
| | 7-(2'-deoxy-2'-methoxy-2'-C-methyl-β-D-ribo-furanosyl)-4-amino-5-nitro-pyrrolo[2,3-d]pyrimidine |
| | 7-(2'-deoxy-2'-methoxy-2'-C-methyl-β-D-ribo-furanosyl)-4-amino-5-(phenyl-acetylenyl)-pyrrolo[2,3-d]py-rimidine |
| | 7-(2'-deoxy-2'-methoxy-2'-C-methyl-β-D-ribo-furanosyl)-4-amino-5-formyl-pyrrolo[2,3-d]pyrimidine |
| | 7-(2'-deoxy-2'-methoxy-2'-C-methyl-β-D-ribo-furanosyl)-4-amino-5-boronic acid-pyrrolo[2,3-d]pyrimidine |

TABLE I-continued

| Compound | Name |
|---|---|
| (structure) | 7-(2'-deoxy-2'-methoxy-2'-C-methyl-β-D-ribo-furanosyl)-4-amino-5-acetylenyl-pyrrolo[2,3-d]pyrimidine |
| (structure) | 7-(2'-deoxy-2'-methoxy-2'-C-methyl-β-D-ribo-furanosyl)-4-amino-5-(tri-methylsilylacetylenyl)-pyrrolo[2,3-d]pyrimidine |
| (structure) | 7-(2'-deoxy-2'-methoxy-2'-C-methyl-β-D-ribo-furanosyl)-4-amino-5-ethenyl-pyrrolo[2,3-d]pyrimidine |
| (structure) | 7-(2'-deoxy-2'-methoxy-2'-C-methyl-β-D-ribo-furanosyl)-4-amino-5-methylenehydrazine-pyrrolo[2,3-d]pyrimidine |
| (structure) | 7-(2'-deoxy-2'-methoxyo-2'-C-methyl-β-D-ribo-furanosyl)-4-amino-5-(carb-aldehyde-oxime)-pyrrolo[2,3-d]pyrimidine(cis/trans or a mixture thereof) |

TABLE I-continued

| Compound | Name |
| --- | --- |
| | 7-(2'-deoxy-2'-methoxy-2'-C-methyl-β-D-ribo-furanosyl)-4-hydroxyamino-5-nitro-pyrrolo[2,3-d]pyrimidine |
| | 7-(2'-deoxy-2'-methoxy-2'-C-methyl-β-D-ribo-furanosyl)-4-hydroxyamino-5-(phenyl-acetylenyl)-pyrrolo[2,3-d]py-rimidine |
| | 7-(2'-deoxy-2'-methoxy-2'-C-methyl-β-D-ribo-furanosyl)-4-hydroxyamino-5-formyl-pyrrolo[2,3-d]pyrimidine |
| | 7-(2'-deoxy-2'-methoxy-2'-C-methyl-β-D-ribo-furanosyl)-4-hydroxyamino-5-boronic acid-pyrrolo[2,3-d]pyrimidine |

TABLE I-continued

| Compound | Name |
|---|---|
| 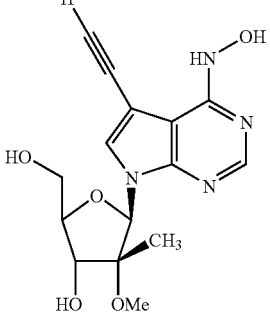 | 7-(2'-deoxy-2'-methoxy-2'-C-methyl-β-D-ribofuranosyl)-4-hydroxyamino-5-acetylenyl-pyrrolo[2,3-d]pyrimidine |
| 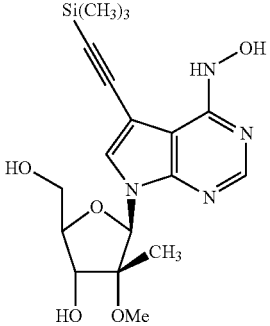 | 7-(2'-deoxy-2'-methoxy-2'-C-methyl-β-D-ribofuranosyl)-4-hydroxyamino-5-(trimethylsilylacetylenyl)-pyrrolo[2,3-d]pyrimidine |
| 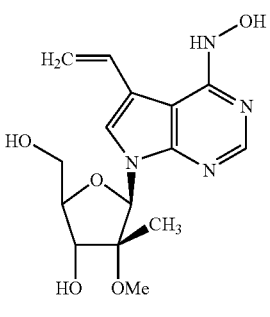 | 7-(2'-deoxy-2'-methoxy-2'-C-methyl-β-D-ribofuranosyl)-4-hydroxyamino-5-ethenyl-pyrrolo[2,3-d]pyrimidine |
| 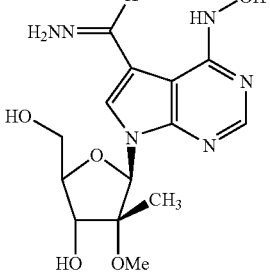 | 7-(2'-deoxy-2'-methoxy-2'-C-methyl-β-D-ribofuranosyl)-4-hydroxyamino-5-methylenehydrazine-pyrrolo[2,3-d]pyrimidine |
| 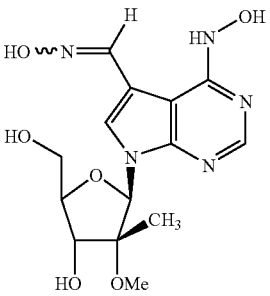 | 7-(2'-deoxy-2'-methoxyo-2'-C-methyl-β-D-ribofuranosyl)-4-hydroxyamino-5-(carbaldehyde-oxime)-pyrrolo[2,3-d]pyrimidine(cis/trans or a mixture thereof) |

TABLE I-continued

| Compound | Name |
|---|---|
| | 7-(2'-deoxy-2'-methoxy-2'-C-methyl-β-D-ribo-furanosyl)-4-acetylamino-5-nitro-pyrrolo[2,3-d]pyrimidine |
| | 7-(2'-deoxy-2'-methoxy-2'-C-methyl-β-D-ribo-furanosyl)-4-acetylamino-5-(phenyl-acetylenyl)-pyrrolo[2,3-d]pyrimidine |
| | 7-(2'-deoxy-2'-methoxy-2'-C-methyl-β-D-ribo-furanosyl)-4-acetylamino-5-formyl-pyrrolo[2,3-d]pyrimidine |
| | 7-(2'-deoxy-2'-methoxy-2'-C-methyl-β-D-ribo-furanosyl)-4-acetylamino-5-boronic acid-pyrrolo[2,3-d]pyrimidine |

TABLE I-continued

| Compound | Name |
|---|---|
| (structure) | 7-(2'-deoxy-2'-methoxy-2'-C-methyl-β-D-ribo-furanosyl)-4-acetylamino-5-acetyl-enyl-pyrrolo[2,3-d]pyrimidine |
| (structure) | 7-(2'-deoxy-2'-methoxy-2'-C-methyl-β-D-ribo-furanosyl)-4-acetylamino-5-(tri-methylsilylacetylenyl)-pyrrolo[2,3-d]pyrimidine |
| (structure) | 7-(2'-deoxy-2'-methoxy-2'-C-methyl-β-D-ribo-furanosyl)-4-acetylamino-5-ethenyl-pyrrolo[2,3-d]pyrimidine |
| (structure) | 7-(2'-deoxy-2'-methoxy-2'-C-methyl-β-D-ribo-furanosyl)-4-acetylamino-5-methylenehydrazine-pyrrolo[2,3-d]pyrimidine |

TABLE I-continued

| Compound | Name |
|---|---|
| | 7-(2'-deoxy-2'-methoxyo-2'-C-methyl-β-D-ribo-furanosyl)-4-acetylamino-5-(carb-aldehyde-oxime)-pyrrolo[2,3-d]pyrimidine(cis/trans or a mixture thereof) |
| | 7-(2'-deoxy-2'-methoxy-2'-C-methyl-β-D-ribo-furanosyl)-4-ethoxyamino-5-nitro-pyrrolo[2,3-d]pyrimidine |
| | 7-(2'-deoxy-2'-methoxy-2'-C-methyl-β-D-ribo-furanosyl)-4-ethoxyamino-5-(phenyl-acetylenyl)-pyrrolo[2,3-d]pyrimidine |
| | 7-(2'-deoxy-2'-methoxy-2'-C-methyl-β-D-ribo-furanosyl)-4-ethoxyamino-5-formyl-pyrrolo[2,3-d]pyrimidine |

TABLE I-continued

| Compound | Name |
|---|---|
| | 7-(2'-deoxy-2'-methoxy-2'-C-methyl-β-D-ribo-furanosyl)-4-ethoxyamino-5-boronic acid-pyrrolo[2,3-d]pyrimidine |
| | 7-(2'-deoxy-2'-methoxy-2'-C-methyl-β-D-ribo-furanosyl)-4-ethoxyamino-5-acetyl-enyl-pyrrolo[2,3-d]pyrimidine |
| | 7-(2'-deoxy-2'-methoxy-2'-C-methyl-β-D-ribo-furanosyl)-4-ethoxyamino-5-(tri-methylsilylacetylenyl)-pyrrolo[2,3-d]pyrimidine |
| | 7-(2'-deoxy-2'-methoxy-2'-C-methyl-β-D-ribo-furanosyl)-4-ethoxyamino-5-ethenyl-pyrrolo[2,3-d]pyrimidine |
| | 7-(2'-deoxy-2'-methoxy-2'-C-methyl-β-D-ribo-furanosyl)-4-ethoxyamino-5-methylenehydrazine-pyrrolo[2,3-d]pyrimidine |

TABLE I-continued

| Compound | Name |
|---|---|
|  | 7-(2'-deoxy-2'-methoxyo-2'-C-methyl-β-D-ribo-furanosyl)-4-ethoxyamino-5-(carb-aldehyde-oxime)-pyrrolo[2,3-d]pyrimidine(cis/trans or a mixture thereof) |
|  | [4-Amino-5-ethynyl-7-(2-deoxy-2-fluoro-2-C-methyl-β-D-ribofuanosyl)-7H-pyrrolo[2,3-d]pyrimidine]5'-triphosphate |
|  | [4-Amino-5-ethynyl-7-(2-deoxy-2-fluoro-2-C-methyl-β-D-ribofuanosyl)-7H-pyrrolo[2,3-d]pyrimidine]5'-[Rp/Sp-Methoxyalaninylphenylphosphate] |
|  | [4-Amino-5-ethynyl-7-(2-deoxy-2-fluoro-2-C-methyl-β-D-ribofuanosyl)-7H-pyrrolo[2,3-d]pyrimidine]5'-L-valyl ester |

TABLE I-continued

| Compound | Name |
|---|---|
|  | [4-Amino-5-ethynyl-7-(2-deoxy-2-fluoro-2-C-methyl-β-D-ribofuanosyl)-7H-pyrrolo[2,3-d]pyrimidine]5'-[Bis(S-pivaloyl-2-thioethyl)phosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Bis(S-(3-methyl-butyryl)-2-thioethyl)phosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-methoxyphenyl)phosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-fluorophenyl)phosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Ethoxyalaninylphenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-methylphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-propylphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-phenylphosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(naphthalen-2-yl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(naphthalen-1-yl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(4-chloro-naphthalen-1-yl)phosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(4-methoxynaphthalen-1-yl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninylphenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-methoxyphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-fluorophenyl)phosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-methylphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyvalinylphenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-methoxyphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-fluorophenyl)phosphate] |

TABLE I-continued

| Compound | Name |
|---|---|
|  | [4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-methylphenyl)phosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Methoxy(dimethylglycyl)phenylphosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Benzyloxydimethylglycinylphenylphosphate] |
|  | [4-Amino-5-ethynyl-7-(2-deoxy-2-fluoro-2-C-methyl-β-D-ribofuanosyl)-7H-pyrrolo[2,3-d]pyrimidine]5'-[Methoxydimethylglycinyl(4-fluorophenyl)phosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Methoxydimethylglycinyl(4-methoxyphenyl)phosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxydimethylglycinylphenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyprolinylphenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Bezyloxyprolinylphenylphosphate] |

TABLE I-continued

| Compound | Name |
|---|---|
| | [4-Amino-5-ethynyl-7-(2-deoxy-2-fluoro-2-C-methyl-β-D-ribofuanosyl)-7H-pyrrolo[2,3-d]pyrimidine]5'-[Methoxyprolinyl(4-fluorophenyl)phenylphosphate] |
| | [4-Amino-5-ethynyl-7-(2-deoxy-2-fluoro-2-C-methyl-β-D-ribofuanosyl)-7H-pyrrolo[2,3-d]pyrimidine]5'-[Methoxyprolinyl(4-methoxyphenyl)phenylphosphate] |

DETAILED DESCRIPTION OF THE INVENTION

The invention is directed to compounds, compositions and methods for treating Flaviviridae viruses, such as hepatitis C virus infections. However, prior to describing this invention in detail, the following terms will first be defined:

DEFINITIONS

Unless otherwise defined, the term "alkyl" refers to hydrocarbyl groups having from 1 to 6 carbon atoms, preferably 1 to 3, and more preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, guanidino, heteroaryl, substituted heteroaryl, heterocyclic, substituted heterocyclic, thiol, and thioalkyl.

Unless otherwise defined, the term "Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Alkoxyalkyl" refers to the groups -alkylene(alkoxy)n and -alkylene(substituted alkoxy), where alkylene is a divalent straight or branched chain alkylene group of from 1 to 3 carbon atoms, alkoxy and substituted alkoxy are as defined herein and n is an integer from 1 to 2.

"Acyl" refers to the groups alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR$^4$R$^4$ where each R$^4$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^4$ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC (O)—, substituted heteroaryl-OC(O)—, heterocyclic-OC(O)—, and substituted heterocyclic-OC(O)—.

"Alkenyl" refers to an unsaturated hydrocarbon having from 2 to 6 carbon atoms and more preferably 2 to 4 carbon atoms and having at least 1 and preferably from 1 to 2 sites of vinyl (>C=C<) unsaturation. Such groups are exemplified by vinyl (ethen-1-yl), allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the term "substituted alkenyl" includes both E (cis) and Z (trans) isomers as appropriate. The isomers can be pure isomeric compounds or mixtures of E and Z components.

"Alkynyl" refers to an unsaturated hydrocarbon having at least 1 site of acetylenic (—C≡C—) unsaturation and having from 2 to 6 carbon atoms and preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Amidino" refers to the group —C(=NR$^{11}$)NR$^{11}$R$^{11}$ where each R$^{11}$ is independently selected from hydrogen or alkyl.

"Aminoacyl" refers to the groups —NR$^5$C(O)alkyl, —NR$^5$C(O)substituted alkyl, —NR$^5$C(O)-cycloalkyl, —NR$^5$C(O)substituted cycloalkyl, —NR$^5$C(O)alkenyl, —NR$^5$C(O)substituted alkenyl, —NR$^5$C(O)alkynyl, —NR$^5$C(O)substituted alkynyl, —NR$^5$C(O)aryl, —NR$^5$C(O)substituted aryl, —NR$^5$C(O)heteroaryl, —NR$^5$C(O)substituted heteroaryl, —NR$^5$C(O)heterocyclic, and —NR$^5$C(O)substituted heterocyclic where R$^5$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amidino, amino, substituted amino, aminoacyl, aryl, substituted aryl, aryloxy, substituted aryloxy, cycloalkoxy, substituted cycloalkoxy, carboxyl, carboxyl ester, cyano, guanidino, oxyacyl, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, hydrazino, and —S(O)$_m$R$^{32}$ where R$^{32}$ is selected from the group consisting of alkyl, substituted alkyl, amino, substituted amino, aryl, substituted aryl, heteroaryl, substituted heteroaryl, heterocyclic and substituted heterocyclic and m is 1 or 2.

A preferred aromatic is a phenyl group which refers to the well known C$_6$H$_5$ (sometimes referred by the Greek letter ϕ (phi)) and is represented by the formula:

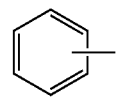

A preferred substituted aryl group is "substituted phenyl" wherein the phenyl group is substituted with 1 to 3 substituents selected from the group consisting of alkyl, substituted alkyl, alkenyl, substituted alkenyl, alkynyl, substituted alkynyl, alkoxy, substituted alkoxy, acyl, acylamino, acyloxy, aminoacyl, amidino, amino, substituted amino, carboxyl, carboxyl ester, cyano, cycloalkyl, substituted cycloalkyl, cycloalkoxy, substituted cycloalkoxy, guanidino, halo, heteroaryl, substituted heteroaryl, hydrazine, hydroxyl, nitro, oxyacyl, thiol, and —S(O)$_y$R$^{32}$ where R$^{32}$ is selected from the group consisting of alkyl, substituted alkyl, amino, substituted amino, aryl, substituted aryl, heteroaryl, substituted heteroaryl, heterocyclic and substituted heterocyclic and y is 0, 1 or 2.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-heterocyclic, —C(O)O-substituted heterocyclic, —C(O)O-heteroaryl, —C(O)O-substituted heteroaryl, —C(O)O-aryl, and —C(O)O-substituted aryl wherein alkyl, substituted alkyl, alkenyl, substituted alkenyl, alkynyl, substituted alkynyl, cycloalkyl, substituted cycloalkyl, heteroaryl, heterocyclic, substituted heterocyclic, substituted heteroaryl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Formyl" refers to the group —C(O)H.

"Carbaldehyde oxime" refers to the group —CH(=N—OH).

"Guanidino" refers to the group —NR$^{12}$C(=NR$^{12}$)NR$^{12}$R$^{12}$ where each R$^{12}$ is independently hydrogen or alkyl.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, and sulfur within the ring wherein the nitrogen and/or sulfur is optionally oxidized [(N→O), —S(O)—, or —SO$_2$—]. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an aromatic ring atom. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted phenyl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen and sulfur within the ring wherein the nitrogen and/or sulfur atoms can be optionally oxidized [(N→O), —S(O)— or —SO$_2$—] and further wherein, in fused ring systems, one or more the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Hydrazino" refers to the group —NR$^{13}$NR$^{13}$R$^{13}$ wherein each R$^{13}$ is independently selected from the group consisting of hydrogen or alkyl.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at the 2, 3, or 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^6$) or salts thereof including partial salts thereof, wherein each R$^6$ is independently selected from hydrogen, alkyl, substituted alkyl, carboxylic acid, and carboxyl ester. It is understood, of course, that the initial oxygen of the phosphonate includes the oxygen atom at the 2, 3, or 5-position of the ribose sugar.

"Phosphorodiamidate" refers to the group:

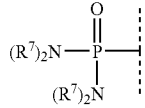

where each R$^7$ may be the same or different and each is hydrogen, alkyl, substituted alkyl, cycloalkyl, or substituted cycloalkyl. A particularly preferred phosphorodiamidate is the following group:

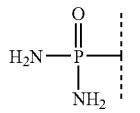

"Phosphoramidate monoester" refers to the group below, where R$^8$ is hydrogen or alkyl; R$^{30}$ is selected from the group consisting of hydrogen, alkyl, substituted alkyl, aryl, substituted aryl, heteroaryl and substituted heteroaryl; and R$^{31}$ is hydrogen or R$^{30}$ together with the carbon atom pendent thereto and R$^{31}$ together with the nitrogen atom pendent thereto join to form a heterocyclic or substituted heterocyclic ring. In a preferred embodiment R$^{30}$ is derived from an L-amino acid.

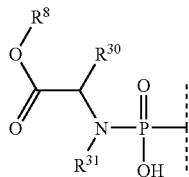

"Phosphoramidate diester" refers to the group below, where R$^8$, R$^{30}$, and R$^{31}$ are as defined above, and R$^9$ is selected from the group consisting of alkyl, substituted alkyl, aryl, substituted aryl, cycloalkyl, substituted cycloalkyl, heteroaryl, substituted heteroaryl, heterocyclic and substituted heterocyclic. In a preferred embodiment $R^{30}$ (and optionally together with $R^{31}$) is derived from an L-amino acid.

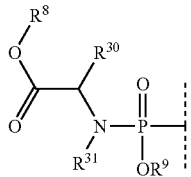

"Cyclic phosphoramidate" refers to the group below, where n is 1 to 3, more preferably n is 1 to 2.

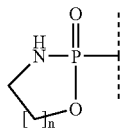

"Cyclic phosphorodiamidate" refers to the group below, where n is 1 to 3, more preferably n is 1 to 2.

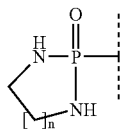

"Phosphonamidate" refers to the group below, where $R^{10}$ is hydrogen, alkyl, substituted alkyl, cycloalkyl, or substituted cycloalkyl.

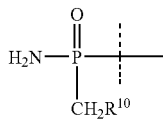

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid sidechain" refers to the $R^{30}$ substituent of α-amino acids of the formula $NHR^{31}CH(R^{30})COOH$ where $R^{31}$ is hydrogen and $R^{30}$ is selected from the group consisting of hydrogen, alkyl, substituted alkyl, aryl and substituted aryl. In the case of proline, $R^{31}$ and $R^{30}$, together with the atoms pendent thereto join to form a pyrrolidone ring. Preferably, the α-amino acid sidechain is the sidechain one of the twenty naturally occurring L amino acids.

The term "pharmaceutically acceptable prodrugs" or "prodrug" refers to art recognized modifications to one or more functional groups which functional groups are metabolized in vivo to provide a compound of this invention or an active metabolite thereof. "Prodrug group" refers to a type of protecting group that, when used to mask a functional group within an active drug, converts the drug into a prodrug. Prodrug groups are typically attached to the functional group of the drug via bonds that are cleavable under specified conditions of use. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like. Examples of prodrug groups include acyl, oxyacyl, phosphonate, phosphate esters, phosphate, phosphonamidate, phosphorodiamidate, phosphoramidate monoester, cyclic phosphoramidate, cyclic phosphorodiamidate, and phosphoramidate diester. Exemplary phosphonate esters include bis-SATE (S-acyl-2-thioethyl)phosponate.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group pendent to a carbon atom of an ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The stereochemistry of each of the furanose stereocenters in the compounds and formulas disclosed in this application are non-racemic and can be depicted in the following equivalent drawings as shown by way of example for formula I:

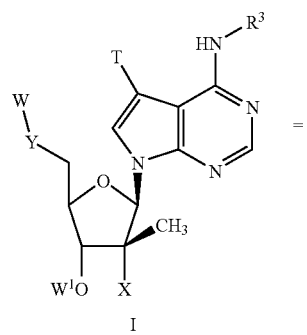

I

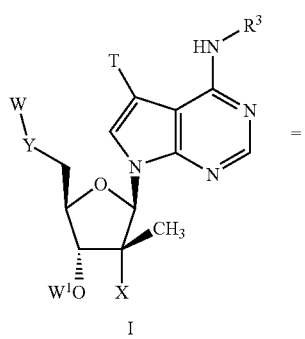

I

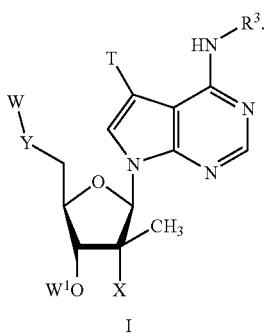

I

The following naming conventions for the compounds disclosed herein are equivalent: 7-(2-deoxy-2-fluoro-2-C-methyl-β-D-ribofuanosyl)-7H-pyrrolo[2,3-d]pyrimidine and 7-(2'-deoxy-2'-fluoro-2'-C-methyl-β-D-ribofuanosyl)-pyrrolo[2,3-d]pyrimidine The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides*," Academic Press, New York, 1963; 2) Goodman L. "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

Strategies available for synthesis of compounds of this invention are illustrated in the synthetic schemes below. In Scheme 1 below, compounds of this invention are prepared from D-ribose.

Scheme 1
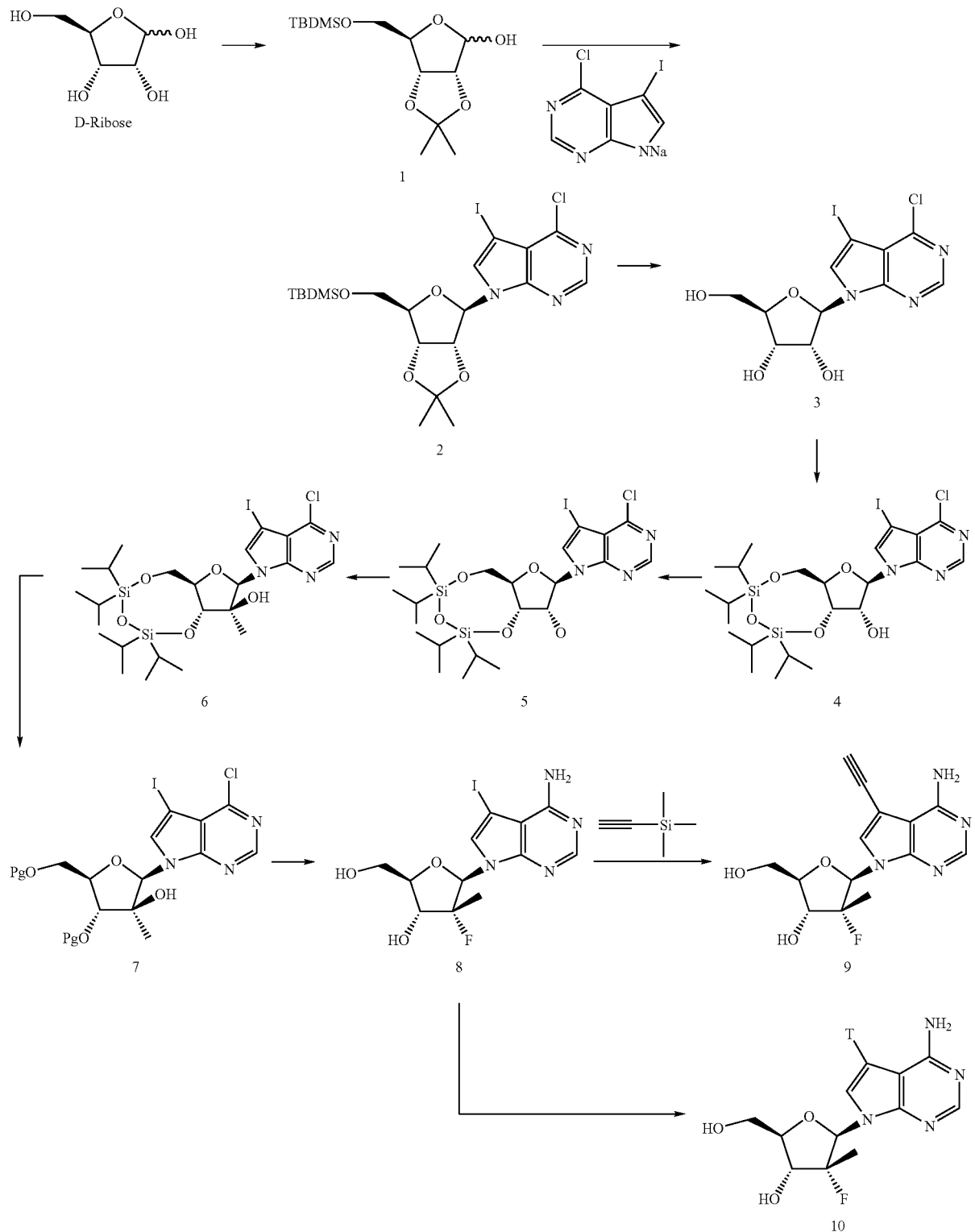
Specifically, the alcohols of ribose may be protected using a variety of known methods prior to coupling with the deazapurine group at the anomeric carbon. In Scheme 1, above, the alcohols at the 2- and 3-position of d-ribose are protected as a cyclic ketal by treatment with acetone under acidic conditions. The alcohol at the 5'-position can then be protected using tert-butyldimethylsilyl (TBDMS) to provide for compound 1. Compound 1 can be isolated by conventional methods such as filtration, evaporation, chromatography, precipitation, and the like or, alternatively, used in the next reaction without purification and/or isolation.

Next, compound 2 is synthesized by coupling compound 1 with the deazapurine shown above. Typically, this reaction takes place by reacting compound 1 with carbon tetrachloride, hexamethylphosphorous triamide/tetrahydrofuan at a temperature from about −70° C. to about −20° C. followed by the addition of the mixture to the deazapurine to provide compound 2. This compound can be isolated by conventional methods such as filtration, evaporation, chromatography, precipitation, and the like or, alternatively, used in the next reaction without purification and/or isolation.

The protecting groups of the hydroxyl groups of compound 2 are removed by conventional methods to provide compound 3. For example, exposure of compound 2 to mild acidic conditions, such as Dowex H+ in methanol, will yield compound 3. Compound 3 can be isolated by conventional methods such as filtration, evaporation, chromatography, precipitation, and the like or, alternatively, used in the next reaction without purification and/or isolation.

Selective protection of the 3,5-dihydroxyl groups of compound 3 proceeds via contact with at least two equivalents of 1,3-dichloro-1,1,3,3,-tetraisopropyldisiloxane (TIPDSCl$_2$) under conditions known in the art to provide for compound 4.

The unprotected 2-hydroxyl group is then oxidized under conventional conditions with one of a number of well known oxidizing agents to provide for compound 5. Possible oxidizing agents include, for example, Dess-Martin periodine reagent, Ac$_2$O+DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO$_2$, ruthenium tetraoxide, phase transfer catalysts such as chromic acid or permanganate supported on a polymer, Cl$_2$-pyridine, H$_2$O$_2$-ammonium molybdate, NaBrO$_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide. The resulting 2-oxo derivative, compound 5, can be isolated by conventional methods such as filtration, evaporation, precipitation, and the like or, alternatively, used in the next reaction without purification and/or isolation.

Conventional methyl Grignard addition to compound 5 occurs from the bottom ("ribo") face due to steric shielding from the nucleobase to yield compound 6. As before, compound 6 can be isolated by conventional methods such as filtration, evaporation, chromatography, precipitation, and the like or, alternatively, used in the next reaction without purification and/or isolation.

The protecting groups of compound 6 are removed by conventional means, such as reacting compound 6 with tetrabutylammonium fluoride. The hydroxyl groups are then selectively protected by adding a protecting group (Pg) such as dihydropyran or benzyl chloride under the appropriate conditions to provide the bis-protected compound 7. Compound 7 can be isolated by conventional methods such as filtration, evaporation, chromatography, precipitation, and the like or, alternatively, used in the next reaction without purification and/or isolation.

Subsequent fluorination with (diethylamino)sulfur trifluoride (DAST) will occur selectively at the 2'-center via an S$_N$2 reaction mechanism resulting in inversion of the stereochemistry of the methyl group at the 2'-carbon atom.

Removal of the 3,5-dihydroxy protecting groups proceeds conventionally using the appropriate conditions to provide compound 8 which can be isolated by conventional methods such as filtration, evaporation, chromatography, precipitation, and the like or, alternatively, used in the next reaction without purification and/or isolation.

As shown in Scheme 1, the iodo group of compound 8 is converted to the corresponding (trimethyl)silylacetylenyl group (compound 27, Example 1) via a conventional Sonogashira coupling reaction in the presence of Pd(0). Specifically, this reaction proceeds by first dissolving compound 8 in a suitable inert diluent such as DMF, THF or a mixture of DMF/THF such as 3:7 ratio. A catalytic amount of both cuprous iodide (CuI) and tetrakis(triphenylphosphine)palladium(0) is then added to the reaction mixture together with an excess, typically 1.1 to 2 equivalents, of (trimethylsilyl)acetylene. The reaction is preferably conducted in the presence of a base such as triethylamine and preferably is conducted under an inert atmosphere. The reaction is typically conducted at from about 10° to about 30° C. and is continued until substantial completion which typically occurs in about 12 to 48 hours.

This compound can then be used to prepare the acetylene derivative (—C≡CH) by desilylation which occurs via conventional methods using ammonium hydroxide, pottasium carbonate or fluoride anions. For example, reaction of the trimethylsilylacetylene compound with ammonium hydroxide in methanol provides for compound 9. Compound 9 can then be isolated by conventional means.

Alternatively, compound 8 can be used as to prepare substituted acetylene derivatives of the formula T, compound 10, in the manner described above and shown in the schemes below.

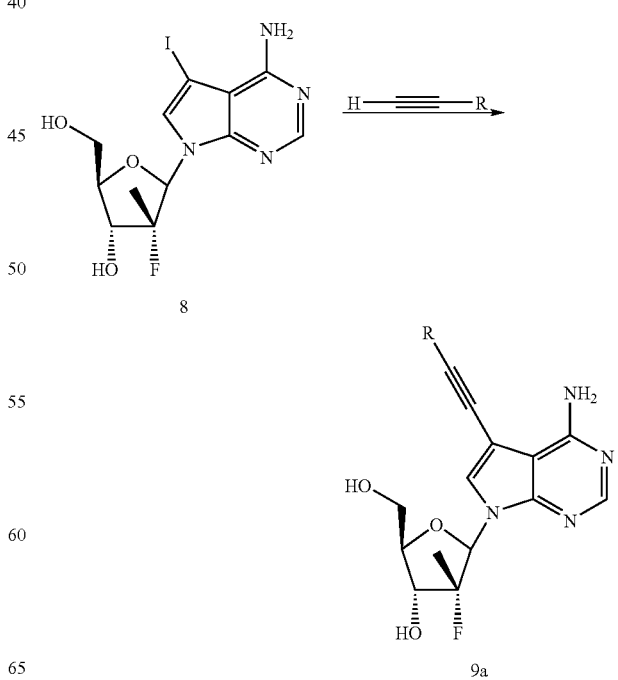

In this embodiment, acetylene compound, HC≡C—R, is substituted for the (trimethyl)silylacetylenyl group in the Sonogashira coupling reaction to provide compound 9a.

Alternatively, certain compounds of the present invention can be prepared as shown in Scheme 3, below, where the 2'-β-methyl-2'-α-fluoro groups are added to the ribose sugar of the already functionalized purine base.

ganate, $MnO_2$, ruthenium tetraoxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide. The resulting 2-oxo derivative, com-

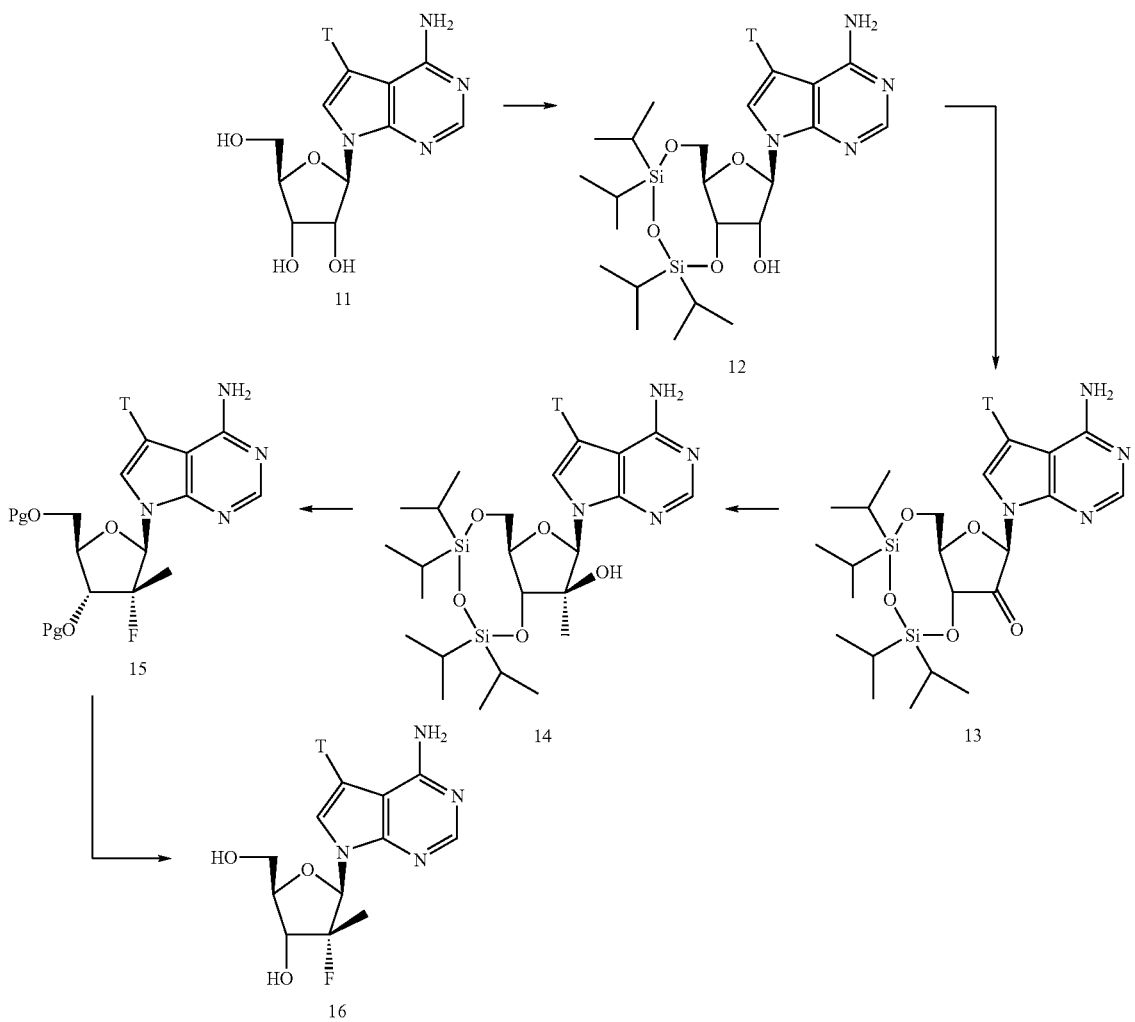

Scheme 3

Specifically, functionalized deazapurine compound 11 is selectively protected at the 3',5'-dihydroxy positions proceeds via contact with approximately two equivalents of 1,3-dichloro-1,1,3,3,-tetraisopropyldisiloxane (TIPDSCl$_2$) under conditions known in the art to provide for compound 12.

The unprotected 2-hydroxyl group is then oxidized under conventional conditions with one of a number of well known oxidizing agents to provide for compound 13. Possible oxidizing agents include, for example, Dess-Martin periodine reagent, Ac$_2$O+DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanpound 13, can be isolated by conventional methods such as filtration, evaporation, chromatography, precipitation, and the like or, alternatively, used in the next reaction without purification and/or isolation.

Conventional methyl Grignard addition to compound 13 occurs from the bottom ("ribo") face due to steric shielding from the nucleobase to yield compound 14. As before, compound 14 can be isolated by conventional methods such as filtration, evaporation, chromatography, precipitation, and the like or, alternatively, used in the next reaction without purification and/or isolation.

The protecting groups of compound 14 are removed by conventional means, such as reacting compound 14 with tetrabutylammonium fluoride. The hydroxyl groups are then selectively protected by adding a protecting group (Pg) such as dihydropyran or benzyl chloride under the appropriate conditions. Subsequent fluorination with (diethylamino)sulfur trifluoride (DAST) will occur selectively at the 2'-center via an $S_N2$ reaction mechanism resulting in inversion of the stereochemistry of the methyl group at the 2-carbon atom to produce compound 15.

Removal of the 3,5-dihydroxy protecting groups proceeds conventionally using the appropriate conditions to provide for compound 16.

Nucleosides the formula of compound 11 can be prepared from substituted purines well known in the art. See, for example, Seela, et al., U.S. Pat. No. 6,479,651 which is incorporated herein by reference in its entirety.

Preparation of compounds where W, $W^1$ or $W^2$ is other than hydrogen, using the compounds prepared above as the starting materials, can be accomplished using the methods described in the following reviews of prodrug preparation:

Cooperwood, J. S. et al., "*Nucleoside and Nucleotide prodrugs,*" in Ed(s).

Chu, C. K. Recent Advances in Nucleosides (2002), 92-147.

Zemlicka, J. et al., Biochimica et Biophysica Acta (2002), 158(2-3), 276-286.

Wagner, C. et al., Medicinal Research Reviews (2002), 20(6), 417-451.

Meier, C. et al., Synlett (1998), (3), 233-242.

For example, conversion of the 5'-hydroxyl group of compound 16 to a phospho, diphospho or triphospho-analog can be prepared using the methods describe in D. W. Hutchinson, (Ed. Leroy b. Townsend) "The Synthesis, reaction and Properties of Nucleoside Mono-, Di-, Tri-, and tertaphosphate and Nucleosides with Changes in the Phosphoryl Residue, "Chemistry of Nucleosides and Nucleotides, Plenum Press, (1991) 2.

The preparation of amino acid esters on the 2'-deoxy-2-β-ribofuranoside can be accomplished as shown in Scheme 4 below:

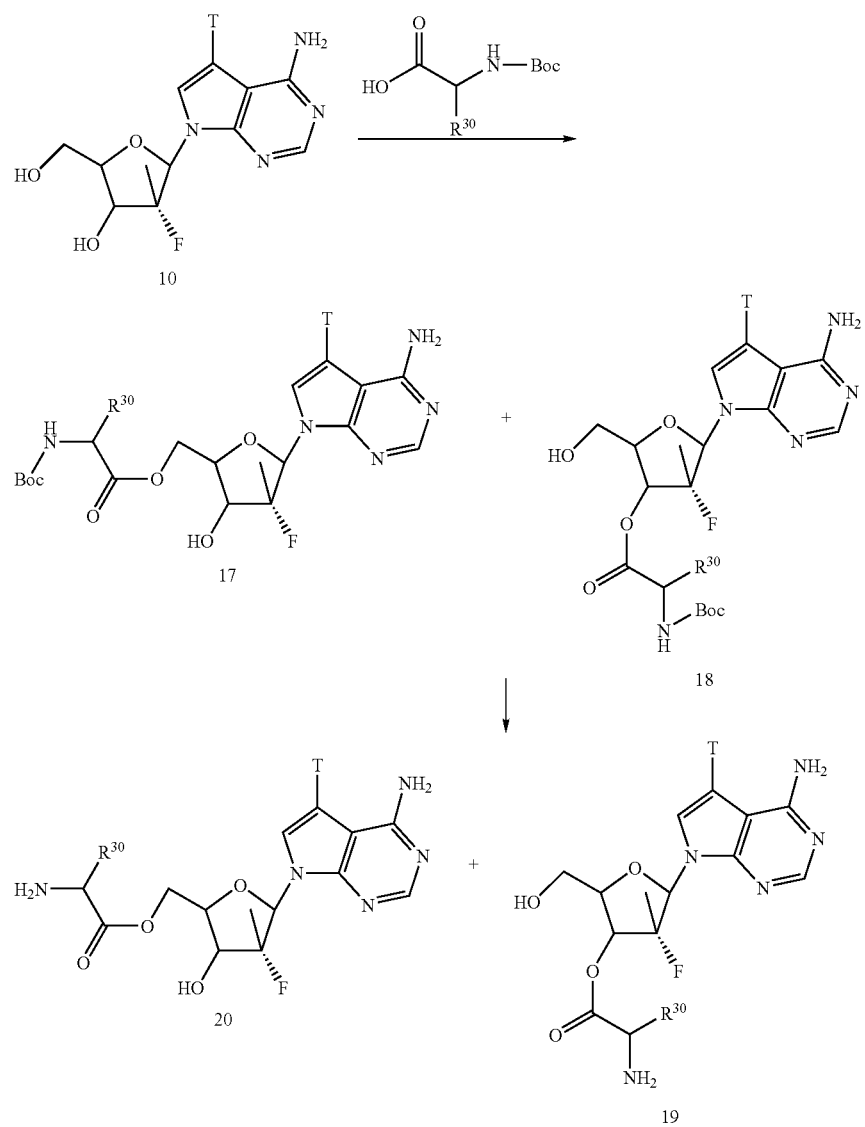

where $R^{30}$ and T are as defined above and Boc is t-butoxycarbonyl.

Specifically, the desired Boc-protected amino acid and N,N'-carbonyldiimidazole are dissolved in an inert solvent such as THF. The reaction mixture is held between about 20 to 40° C. for about 0.5 to 24 hours. A solution containing a slight excess of the desired nucleoside, compound 10, in an inert solvent such as DMF, is added to the Boc-protected amino acid mixture and is heated at about 40 to about 80° C. for about 2 to about 24 hours. A mixture of structural isomers, compounds 17 and 18, is obtained. The mixture can then be isolated and separated using conventional techniques such as evaporation, precipitation, filtration, crystallization, chromatography and the like. Alternatively, the mixture can be used in the next step without further purification.

The Boc protecting group of compounds 17 and 18 is removed under acid conditions using, for example, 1:1 v/v TFA/DCM solution for about 0.1 to about 1 hour at about 20 and about 40° C. The solvent is then evaporated and the residue is dissolved in water and held at about 0 to about 30° C. for about 2 to about 24 hours. The mixture of compounds 19 and 20 can be separated and the desired product isolated by RP-HPLC using standard techniques and conditions.

Formation of esters at the 3' or 5'-positions of the 2'-deoxyribose nucleoside can be achieved by selective protection of one or the other of these hydroxyl groups as shown in Scheme 5 below. For illustrative purposes, Scheme 5 depicts acylation at the 3'-position.

where T is as defined above.

Specifically, in Scheme 5, compound 10 is dissolved in a dry solvent, such as pyridine, and a silylhalide, such as tert-butylchlorodiphenylsilane, is added to form a protecting group at the 5'-position on the sugar. Any protecting group which can be directed to the 5'-position and can be removed orthogonally to the final desired 3'-ester can be used. This reaction is run for about 4 to 24 hours at a temperature of about 10 to 40° C. The desired acyl chloride is added to the protected nucleoside, compound 21, under conventional ester forming conditions to provide for compound 22 which can be isolated and purified using standard techniques such as isolation, crystallization, extraction, filtration, chromatography and the like or, alternatively, used in the next step without isolation and/or purification. Compound 23 is prepared by removing the protecting group at the 5'-position. This can be accomplished, for example, by reacting compound 22 with a 1 M solution of tetrabutylammonium fluoride (TBAF) in THF. The final product is isolated and purified using standard techniques such as isolation, crystallization, extraction, filtration, chromatography and the like.

Alternatively, acylation at the 5'-hydroxy group of compound 10 proceeds as shown in Scheme 6 below.

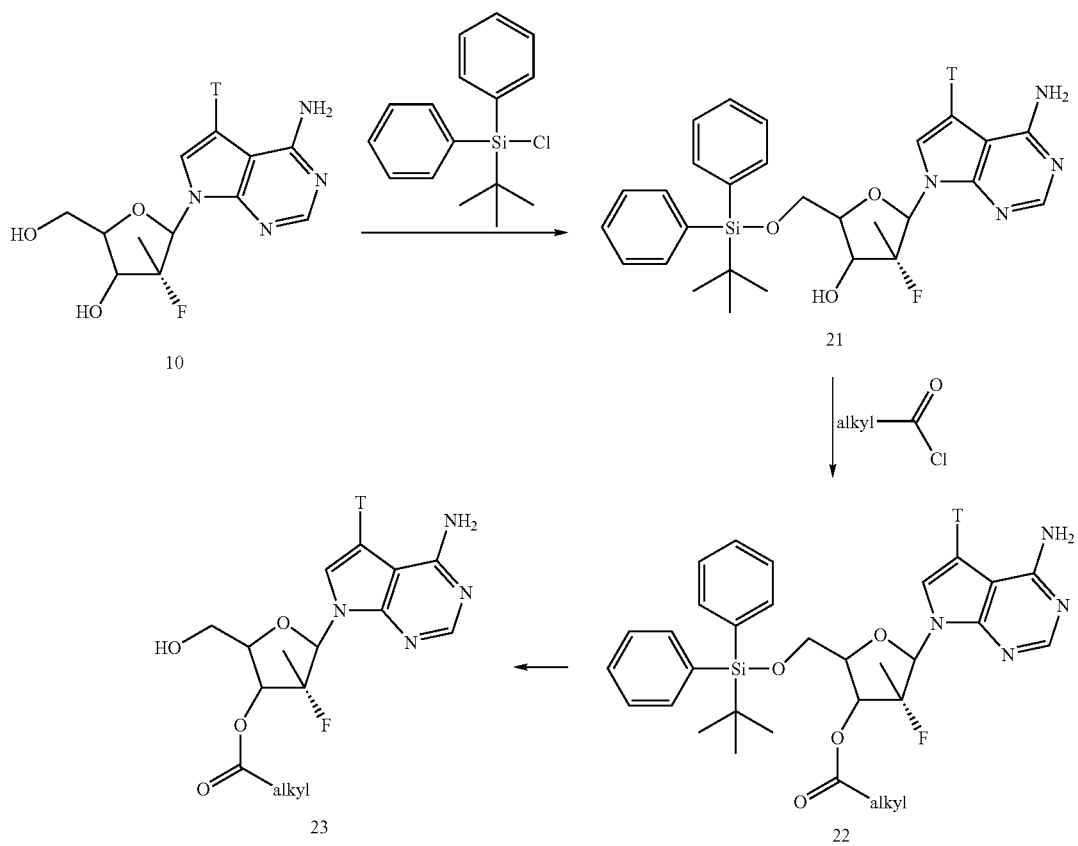

Scheme 5

Scheme 6

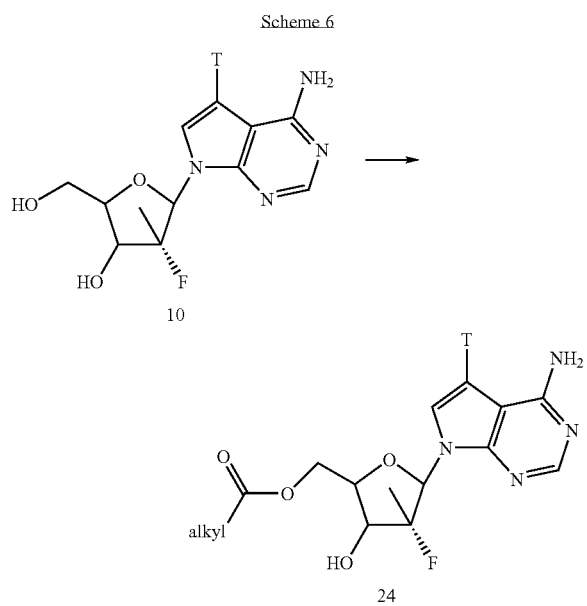

where T is as defined above.

Specifically, in Scheme 6, the primary hydroxy group can be selectively acetylated compound 24 can be obtained by conventional acylation conditions utilizing a suitable acyl chloride. Compound 24 can be isolated and purified using standard techniques such as isolation, crystallization, extraction, filtration, chromatography and the like or, alternatively, used in the next step without isolation and/or purification.

The synthesis of other compounds of this invention follows the procedures set froth above using chemistry well known in the art.

The present invention provides novel compounds possessing antiviral activity, including hepatitis C virus. The compounds of this invention inhibit viral replication by inhibiting the enzymes involved in replication, including RNA dependent RNA polymerase. They may also inhibit other enzymes utilized in the activity or proliferation of viruses in the Flaviviridae family, such as HCV.

The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention may be used alone or in combination with other compounds to treat viruses.

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds of Formula I may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula I based on the total formulation, with the balance being one or more suitable pharmaceutical excipients. Preferably, the compound is present at a level of about 1-80 wt %. Representative pharmaceutical formulations containing a compound of Formula I are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety.

Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharamceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine(Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-5703 10 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of formula 1 and interferon. In some aspects, the interferon is selected from the group consisting of interferon alpha 2B, pegylated interferon alpha, consensus interferon, interferon alpha 2A, and lymphoblastiod interferon tau.

In other embodiments the compositions and methods of the present invention contain a compound of formula 1 and a compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5' monophospate dehydrogenase inhibitor, amantadine, and rimantadine.

EXAMPLES

The examples below as well as throughout the application, the following abbreviations have the following meanings. If not defined, the terms have their generally accepted meanings.

atm=atmospheres
cm=centimeter
DMF=dimethylformamide
DMSO=dimethylsulfoxide
eq.=equivalents
g=gram
HPLC=high pressure liquid chromatography
KOAc=potassium acetate
L=liter
mg=milligram
mL=milliliter
mmol=millimole
q.s.=suitable quantity
TEA=triethylamine
THF=tetrahydrofuran
TLC=thin layer chromatography
v/v=volume/volume
µL=microliter Example 1

Preparation of 4-amino-5-ethynyl-7-(2-deoxy-2-fluoro-2-C-methyl-B-D-ribofuanosyl)-7H-pyrrolo[2,3-d]pyrimidine

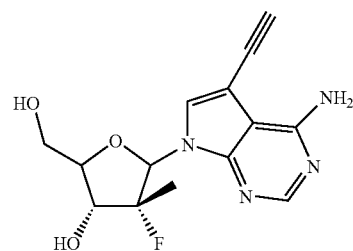

Step 1. 2,3-O-Isopropylidene-D-ribofuranose

Into a suspension of D-ribose (50 g, 0.33 mol) in acetone (1500 mL) was added sulphuric acid (1 mL) dropwise. Reaction mixture was stirred overnight at room temperature and then neutralized with sat. aq. NaHCO₃. Solution was decanted and concentrated. Oily residue was dissolved in EtOAc (1000 mL) and washed with water (300 mL). Aqueous layer was re-extracted with EtOAc (2×500 mL). Combined extracts were dried over Na$_2$SO$_4$ and concentrated to yield the target compound (42.3 g, 67.3%) as oil which was used as such for the next step.

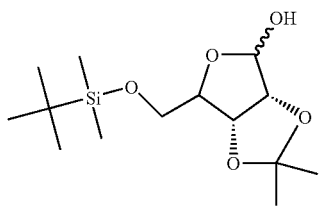

Step 2. 5-O-tert-Butyldimethylsily-2,3-O-isopropylidene-D-ribofuranose 2,3-O-isopropylidene-D-ribofuranose, obtained as described above (21.7 g, 0.114 mol) was dissolved in anhydrous CH$_2$Cl$_2$ (600 mL) and imidazole (15.53 g, 0.228 mol) and TBDMSCl (18.90 g, 0.125 mol) were added under argon. After stirring for 3 h at room temperature reaction mixture was neutralized with 1 N aq. HCl. Two layers were separated. Organic layer was washed with water and saturated brine, dried (Na$_2$SO$_4$) and evaporated. Residue was purified on silica gel column with hexanes/EtOAc (11/1, 1800 mL; 10/1, 1540 mL; 8/1, 1800 mL) as the eluents to yield 23.89 g (69%) of the target compound (as mixture of alp isomers 88/12) as a thick oil (which slowly crystallized in the freezer).

$^1$H NMR (DMSO-d$_6$): δ 6.39 (d, 1H, J=4.4 Hz), 5.11 (d, 1H, J=4.4 Hz), 4.56 (d, 1H, J=6.2 Hz), 4.39 (d, 1H, J=6.7 Hz), 3.89 (t, 1H, J=6.7 Hz), 3.52 (m, 2H), 1.31 (s, 3H), 1.19 (s, 3H), 0.82 (s, 9H), 0.00 (s, 6H).

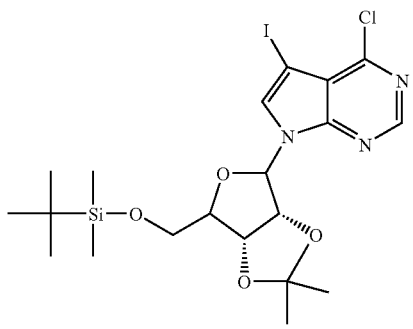

Step 3. 7-(5-O-tert-Butyldimethylsily-2,3-O-isopropylidene-β-D-ribofuranosyl)-4-chloro-5-iodo-7H-pyrrolo[2,3-d]pyrimidine 4-Chloro-5-iodo-7H-pyrrolo[2,3-d]pyrimidine, obtained as described in Example JK-1, Step 1 (14.80 g, 53 mmol) was suspended in anhydrous CH$_3$CN (500 mL). NaH (2.12 g, 53 mmol 60% in oil) was added then and the reaction mixture was stirred at room temperature for 2 h. 5-O-tert-Butyldimethylsily-2,3-O-isopropylidene-D-ribofuranose (15.22 g, 50 mmol), obtained as described in Step 2 was dissolved in anhydrous THF (100 mL), CCl4 (6.27 mL, 65 mmol) was added and the resulting mixture cooled down to −78° C. At this point HMPT (9.54 mL, 62.5 mmol) was added dropwise. Reaction mixture was allowed to warm slowly (in 0.5 h) to −30° C. and stirred at −30° C. to −20° C. for 1 h and then transferred via canula into the solution of Na-salt of the base. The combined mixture was stirred overnight at room temperature, then filtered and filtrate evaporated. The residue was purified on silica gel with hexanes/EtOAc (15/1) as the eluent to yield the target compound as off-white crisp foam (8.49 g, 30%).

$^1$H NMR (DMSO-d$_6$): δ 8.66 (s, 1H), 8.05 (s, 1H), 6.31 (d, 1H, J=2.6 Hz), 5.16 (dd, 1H, J=6.2, 2.3 Hz), 4.88 (dd, 1H, J=6.2, 2.9 Hz), 4.23 (m, 1H), 3.76 (dd, 2H, J=11.4, 4.1 Hz), 3.67 (dd, 1H, J=11.3, 4.8 Hz), 1.52 (s, 3H), 1.30 (s, 3H), 0.81 (s, 9H), 0.00 (s, 6H).

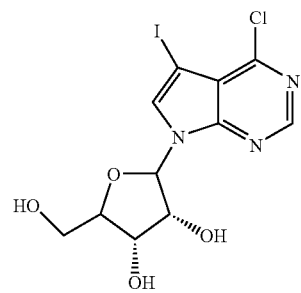

Step 4. 4-Chloro-5-iodo-7-(β-D-ribofuranosyl)-7H-pyrrolo[2,3-d]pyrimidine

To the mixture of the compound from the previous step (5.5 g, 9.7 mmol) in methanol (250 mL) was added Dowex H$^+$ (~20 mL; previously washed with MeOH). The mixture was stirred at room temperature for 3 h. The resin was filtered and washed with methanol (500 mL). The combined filtrates were evaporated and solid residue treated with MeOH (100 mL) to yield after filtration 2.88 g (72%) of the target compound.

$^1$H NMR (DMSO-d$_6$): δ 8.65 (s, 1H), 8.23 (s, 1H), 6.18 (d, 1H, J=6.2 Hz), 5.43 (br, 1H), 5.0-5.3 (br, 2H), 4.36 (m, 1H), 4.08 (dd, 1H, J=5.0, 3.2 Hz), 3.92 (m, 1H), 3.64 (dd, 1H, J=12.0, 3.8 Hz). 3.55 (dd, 1H, J=11.9, 3.7 Hz).

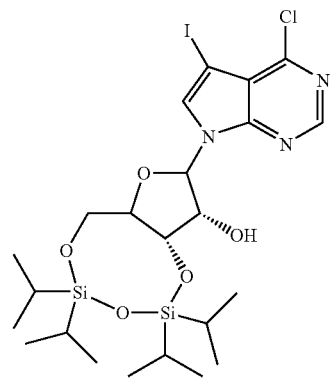

Step 5. 4-Chloro-5-iodo-7-[5,3-O-(1,1,3,3-tetraisopropyldisiloxane-1,3-diyl)-β-D-ribofuranosyl]-7H-pyrrolo[2,3-d]pyrimidine To the solution of nucleoside from the previous step (2.84 g, 6.9 mmol) in pyridine (50 mL) was added TIPDSCl$_2$ (2.2 mL, 6.9 mmol). The resulting mixture was stirred overnight at room temperature. Pyridinium chloride was filtered off and filtrate concentrated. The oily residue was partitioned between saturated aq. NaHCO$_3$ (50 mL) and EtOAc (100 mL). Organic layer was washed with water, saturated brine and dried (Na$_2$SO$_4$). Purification on silica gel with hexanes/EtOAc (9/1, 7/1) as the eluents yielded the target compound as off-white foam (3.67, 81%).

$^1$H NMR (Acetone-d$_6$): δ 8.60 (s, 1H), 7.96 (s, 1H), 6.25 (d, 1H, J=1.2 Hz), 4.74 (dd, 1H, J=4.7 and 8.2 Hz), 4.72 (d, 1H, J=3.2 Hz), 4.54 (m, 1H), 4.28-4.09 (m, 3H), 1.20-1.04 (m, 28H).

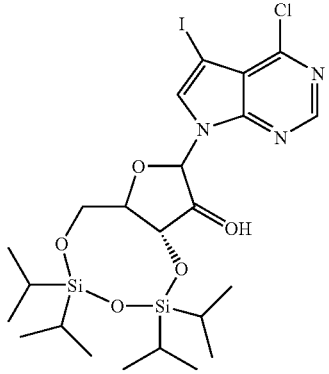

Step 6

Into a well stirred mixture of Dess-Martin periodinane (7.14 g, 16.83 mmol) in CH$_2$Cl$_2$ (80 mL) 80 at 0° C. was added solution of nucleoside from previous step (3.67 g, 5.61 mmol) in CH$_2$Cl$_2$ (20 mL). Reaction mixture was sirred at 0° C. for 0.5 h and 2 d at room temperature then diluted with Et$_2$O (150 mL) and poured into ice-cold mixture of Na$_2$S$_2$O$_3$ (38 g) in sat. aq. NaHCO$_3$ (300 mL). The resulting mixture was vigorously stirred for 15 min. and then layers separated. Organic layer was washed with water, sat. brine, dried (Na$_2$SO$_4$), and evaporated. The crude residue was kept overnight in high vacuum and used as such (3.30 g, 90%) for the next step.

$^1$H NMR (Acetone-d$_6$): δ 8.52 (s, 1H), 8.02 (s, 1H), 6.16 (s, 1H), 5.48 (m, 1H), 4.26-4.20 (m, 3H), 1.22-1.09 (2m, 28H).

MeMgBr (6.7 mL, 20.1 mmol; 3 M in Et$_2$O). After 8 h stirring at −78° C. the reaction was quenched by adding aq. NH$_4$Cl (25 mL, 1 M) and cooling bath was removed. Upon warming to room temperature the mixture was diluted with water and extracted with EtOAc (200+100 mL). Combined extract was washed with water, sat. brine, dried (Na$_2$SO$_4$), and evaporated to off-white solid (3.24 g, 96%) which was used for the next step without further purification.

$^1$H NMR (Acetone-d$_6$): δ 8.58 (s, 1H), 7.93 (s, 1H), 6.31 (s 1H), 4.51 (d, 1H, J=7.8 Hz), 4.16 (m, 2H), 3.93 (m, 1H), 1.54 (s, 3H), 1.23-1.08 (m, 28H).

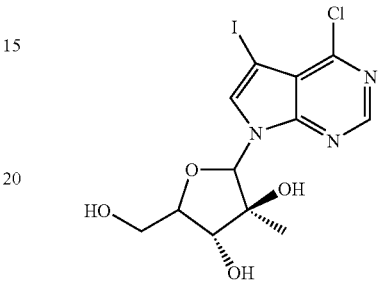

Step 8. 4-Chloro-5-iodo-7-(2-C-methyl-β-D-arabinofuranosyl)-7H-pyrrolo[2,3-d]pyrimidine Into an ice-cold solution of the compound from Step 7 (3.24 g) in THF (50 mL) was added TBAF (9.8 mL, 9.8 mmol; 1 M/THF). The resulting mixture was stirred at 0° C. for 1 h then diluted with MeOH and concentrated. The crude residue was purified on silica gel column with CH$_2$Cl$_2$/MeOH (50/1, 20/1) as the eluents. Fractions containing product were evaporated and residue treated with CH$_2$Cl$_2$ to yield off-white solid (1.35 g, 65%).

$^1$H NMR (DMSO-d$_6$): δ 8.63 (s, 1H), 8.03 (s, 1H), 6.21 (s, 1H), 5.56 (d, 1H, J=5.3 Hz), 5.30 (1H, t, J=5.3 Hz), 5.27 (s, 1H), 3.90 (m, 1H), 3.80 (m, 1H), 3.69 (m, 2H), 1.16 (s, 3H).

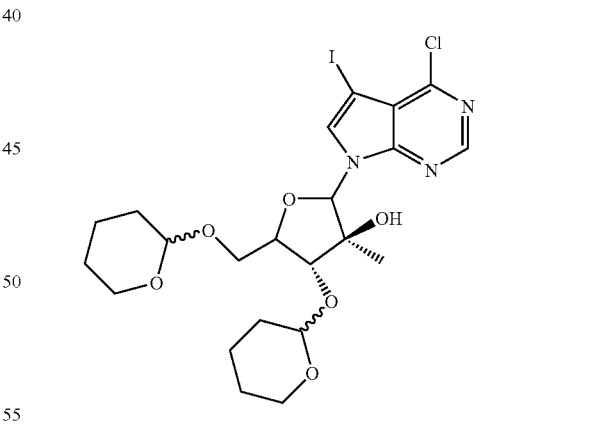

Step 9. 4-Chloro-5-iodo-7-[5,3-di-O-(tetrahydro-2-pyranyl)-2-C-methyl-β-D-arabinofuranosyl]-7H-pyrrolo[2,3-d]pyrimidine Into an ice-cold solution of the product from previous step (1.6 g, 3.75 mmol) in DMF (15 mL) and 3,4-dihydro-2H-pyrane (1.7 mL, 18.75 mmol) was added p-toluenesulfonic acid hydrate (1.425 g, 7.5 mmol) and the solution was stirred 1 d at room temperature. After neutralization with Et$_3$N (3 mL) at 0° C. the mixture was concentrated and purified on silica gel column with hexanes/EtOAc (3/1) to yielded 1.3 g (60%) of the title compound.

Step 7. 4-Chloro-5-iodo-7-[5,3-O-(1,1,3,3-tetraisopropyldisiloxane-1,3-diyl)-2-C-methyl-β-D-arabinofuranosyl]-7H-pyrrolo[2,3-d]pyrimidine To the solution of nucleoside from previous step (3.30 g, 5.06 mmol) in Et$_2$O (40 mL) at −78° C. was added dropwise

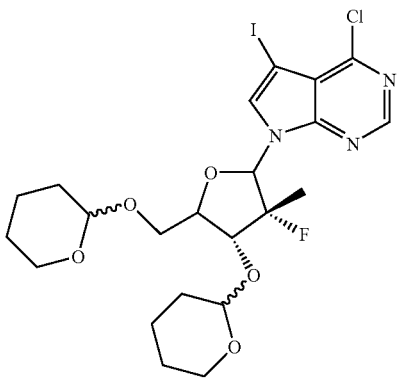

Step 10. 4-Chloro-5-iodo-7-[5,3-di-O-(tetrahydro-2-pyranyl)-2-deoxy-2-fluoro-2-C-methyl-β-D-ribofuranosyl]-7H-pyrrolo[2,3-d]pyrimidine To a cold solution (−20° C.) of the product from previous step (1.15 g, 1.94 mmol) in a mixture of CH$_2$Cl$_2$ (20 mL) and pyridine (2 mL) was added DAST (0.38 mL, 2.9 mmol) dropwise under Ar atmosphere. After 0.5 h at room temperature the solution was poured into sat. aq. NaHCO$_3$ (20 mL) with stirring. The organic layer was washed with water, sat. brine and dried (Na$_2$SO$_4$). Purification on silica gel column with hexanes/EtOAc (9/1, 8/1) yielded 330 mg (30%) of the title compound.

$^{19}$F NMR (Acetone-d$_6$): δ −161.55 (m) MS: m/z 596 (M+1)

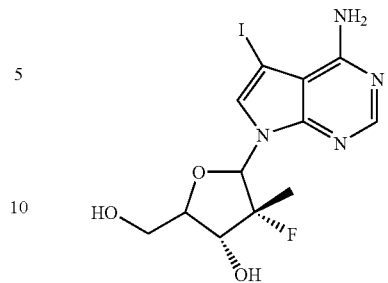

Step 12. 4-Amino-5-iodo-7-(2-deoxy-2-fluoro-2-C-methyl-β-D-ribofuranosyl)-7H-pyrrolo[2,3-d]pyrimidine The nucleoside prepared as described above (155 mg, 0.38 mmol) was treated with liquid ammonia at 90° C. for 12 hours in the high pressure metal reactor. After evaporation of ammonia the residue was purified on silica gel with CH$_2$Cl$_2$/MeOH (30/1, 20/1) +0.1% Et$_3$N as the eluents to yield the target compound as white powder (135 mg, 77%).

$^1$H NMR (Acetone-d$_6$): δ 8.14 (s, 1H), 7.84 (s, 1H), 6.43 (d, 1H, J$_{H-F}$=18.2 Hz), 6.37 (br, 2H), 4.65 (d, 1H, J=8.8 Hz), 4.59 (m, 1H), 4.39 (dm, 1H, J$_{H-F}$=24.3 Hz), 4.05 (2m, 2H), 3.89 (m, 1H), 1.07 (d, 3H, J$_{H-F}$=22.3 Hz). $^{19}$F NMR (Acetone-d$_6$): δ −162.82 (m) MS: m/z 409 (M+1)

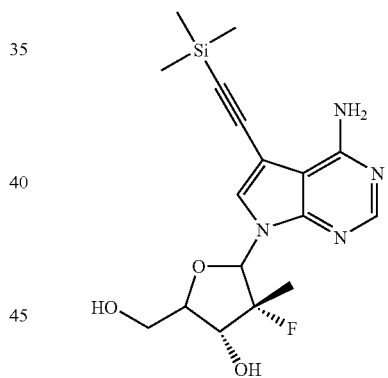

Step 11. 4-Chloro-5-iodo-7-(2-deoxy-2-fluoro-2-C-methyl-β-D-ribofuranosyl)-7H-pyrrolo[2,3-d]pyrimidine A solution of the product from previous step (330 mg, 0.56 mmol) in EtOH (17 mL) was stirred with pyridinium p-toluenesulfonate (281 mg, 1.12 mmol) at 50° C. for 5 h. The reaction mixture was concentrated then and purified on silica gel column with CH$_2$Cl$_2$/MeOH (100/1) to yield the title compound as a white solid (200 mg, 84%).

$^1$H NMR (Acetone-d$_6$): δ 8.65 (s, 1H), 7.89 (s, 1H), 6.56 (d, 1H, J$_{H-F}$=17.3 Hz), 4.74 (dd, 1H, J=8.2 and 0.6 Hz), 4.64 (t, 1H, J=5.0 Hz), 4.42 (dm, 1H, J$_{H-F}$=24.3 Hz), 4.15-4.08 (m, 2H), 3.83 (m, 1H), 1.11 (d, 3H, J$_{H-F}$=22.3 Hz). $^{19}$F NMR (Acetone-d$_6$): δ −163.47 (m)

Step 13. 4-Amino-7-(2-deoxy-2-fluoro-2-C-methyl-β-D-ribofuranosyl)-5-(2-trimethylsilylethynyl)-7H-pyrrolo[2,3-d]pyrimidine To a degassed solution of the product from previous step 70 mg (0.17 mmol) in DMF (6 mL) was added CuI (8 mg, 0.043 mmol), Et$_3$N (24 μL, 0.17 mmol), Pd(PPh$_3$)$_4$ (20 mg, 0.017 mmol), and dropwise trimethylsilyacetilene (36 μL, 0.26 mmol). The reaction mixture was stirred overnight at room temperature then diluted with MeOH and concentrated. Crude residue was purified on silica gel with CH$_2$Cl$_2$/MeOH (50/1, 40/1) as the eluent to afford 56 mg (87%) of the title compound.

$^1$H NMR (Acetone-d$_6$): δ 8.14 (s, 1H), 7.86 (s, 1H), 6.41 (d, 1H, J$_{H-F}$=18.2 Hz), 6.31 (br, 2H), 4.63 (d, 1H, J=8.5 Hz), 4.57 (t, 1H, J=5.4 Hz), 4.40 (dm, 1H, J$_{H-F}$=24.6 Hz), 4.05 (2m, 2H), 3.89 (m, 1H), 1.07 (d, 3H, $J_{H-F}$=22.3 Hz), 0.26 (s, 9H). $^{19}$F NMR (Acetone-d$_6$): δ −162.83 (m) MS: m/z 379 (M+1)

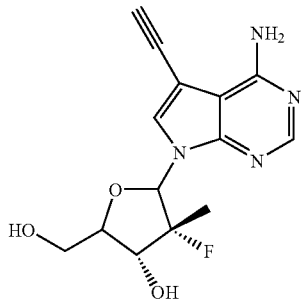

Step 14. 4-Amino-5-ethynyl-7-(2-deoxy-2-fluoro-2-C-methyl-β-D-ribofuanosyl)-7H-pyrrolo[2,3-d]pyrimidine A solution of the product from previous step (55 mg, 0.15 mmol) in MeOH saturated with K$_2$CO$_3$ (20 mL) was stirred at room temperature for 5 min. Purification of the evaporated residue on silica gel column with CH$_2$Cl$_2$/MeOH (30/1) yielded the target compound as a white powder (33 mg, 72%).

$^1$H NMR (DMSO-d$_6$): δ 8.13 (s, 1H), 7.89 (s, 1H), 6.7 (br, 2H), 6.30 (d, 1H, $J_{H-F}$=17.9 Hz), 5.64 (d, 1H, J=7.3 Hz), 5.29 (t, 1H, J=4.8 Hz), 4.29 (s, 1H), 4.11 (m, 1H), 3.86 (m, 2H), 3.67 (m, 1H), 0.95 (d, 3H, $J_{H-F}$=22.5 Hz). $^{19}$F NMR (DMSO-d$_6$): δ −161.04 (m) MS: m/z 307 (M+1).

Example 2

Preparation of 7-(2'-deoxy-2'-fluoro-2'-C-methyl-β-D-ribofuranosyl)-4-amino-5-(2-ethyl carboxylethyn-1yl)-pyrrolo[2,3-d]pyrimidine (Compound 28) and 7-(2'-deoxy-2'-fluoro-2'-C-methyl-β-D-ribofuranosyl)-4-amino-5-(2-carboxamidoethyn-1yl)-pyrrolo[2,3-d]pyrimidine (Compound 29)

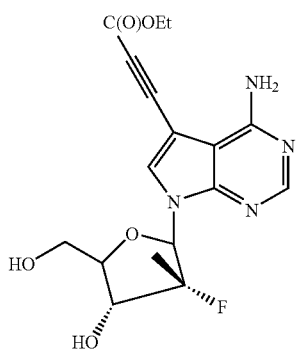

28

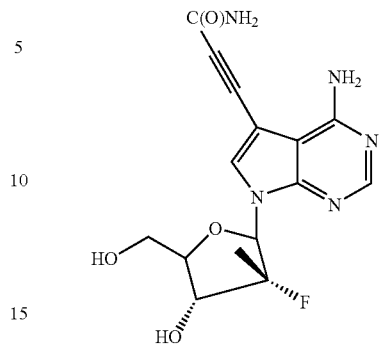

29

To a solution of 7-(2'-fluoro-2'-methyl-β-D-ribofuranosyl)-4-amino-5-iodo-pyrrolo[2,3-d]pyrimidine, compound 8, (450.0 mg, ~1.11 mmol) in 28.8 mL THF-DMF (2:1 v/v) is added CuI (0.082 g, 0.432 mmol), TEA (144 μL, 1.035 mmol), tetrakis(triphenyl-phosphine)palladium(0) (0.126 g, 0.108 mmol) and the solution is degassed with argon. Ethyl propiolate (100 μL, 1.011 mmol) is added and the reaction is heated to 55° C. An additional 100 μL of ethyl propiolate is added every hour for six hours until no starting material is present by TLC. The reaction mixture is concentrated in vacuo, taken up in DMF and recovered by conventional means to provide for compound 28.

Compound 28 (20 mg, ~0.05 mmol) is added 1.0 mL concentrated ammonia solution (30% aqueous solution) and is stirred at room temperature for 1 hour. The resulting precipitate is filtered and dried via co-evaporation with ethanol to yield compound 29.

Example 3

Preparation of 7-(2'-deoxy-2'-fluoro-2'-C-methyl-β-D-ribofuranosyl)-4-amino-5-(ethen-1-yl)-pyrrolo[2,3-d]pyrimidine (Compound 30)

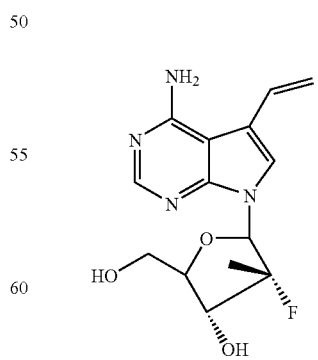

Compound 9 is dissolved in 3 mL THF and 22 mg of Lindlar's catalyst is added. The solution is stirred at ambient temperature under 1 atm of hydrogen (via balloon) for 7 days. The balloon is recharged with hydrogen at the beginning of each day. After 7 days, the reaction is filtered through celite to remove catalyst, concentrated in vacuo, and purified to provide for compound 30.

Example 4

Preparation of 7-(2'-deoxy-2'-fluoro-2'-C-methyl-β-D-ribofuranosyl)-4-amino-5-(formyl)-pyrrolo[2,3-d]pyrimidine (Compound 31)

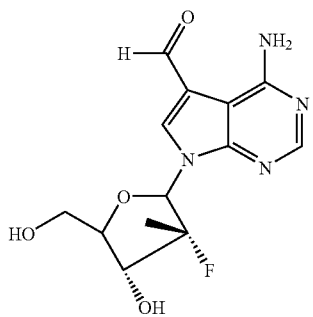

A solution of compound 8 (50.0 mg, ~0.12 mmol) is dissolved in 5 mL dry tetrahydrofuran, which is then purged of air by slowly bubbling with carbon monoxide. To this solution is added tetrakis (triphenylphosphine)palladium(0) (2.8 mg, 0.0025 mmol). The reaction is stirred for 10 minutes, and is then heated to 50° C. Next, tributyltin hydride in THF (35.9 μL, 0.1354 mmol) is slowly added over 2.5 hours—CO gas being continually bubbled through during this time. Upon completion, the mixture is concentrated in vacuo. The reaction crude is dissolved in 1 mL dimethylformamide, is diluted to 50 mL with deionized water, and then is washed through a celite pad. The solution is again concentrated down to dryness then redissolved in 1.0 mL dimethylformamide and 3.5 mL water and is then purified by HPLC to provide for compound 31.

Example 5

Preparation of 7-(2'-deoxy-2'-fluoro-2'-C-methyl-β-D-ribofuranosyl)-4-amino-5-(boronic acid)-pyrrolo[2,3-d]pyrimidine (Compound 32)

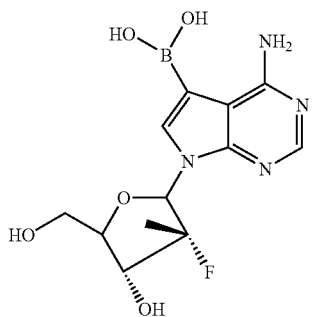

To a solution of compound 8 (60 mg, 0.148 mmol) in 1 mL DMSO is added KOAc (44 mg, 0.449 mmol) and bis(neopentyl glycoloto)diboron (40 mg, 0.177 mmol). The mixture is degassed with argon and $P(Ph_3)_2PdCl_2$ (3.1 mg, 0.004 mmol) is added and the reaction is heated to 80° C. for 4 hours. The mixture is diluted with water compound 32 is recovered by conventional methods.

Example 6

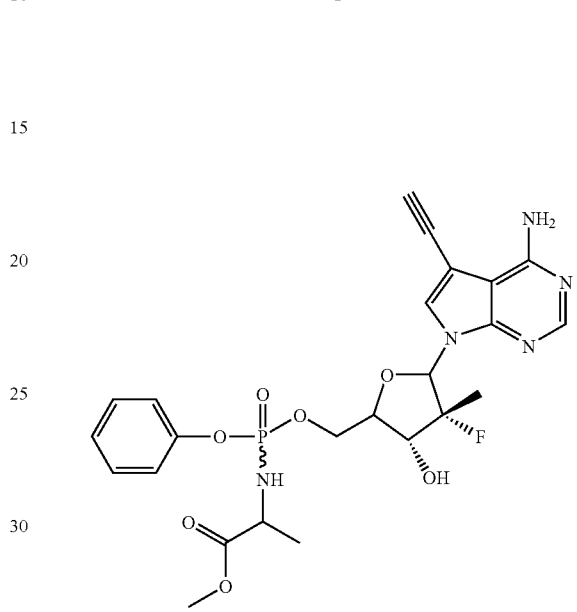

[4-Amino-5-ethynyl-7-(2-deoxy-2-fluoro-2-C-methyl-β-D-ribofuanosyl)-7H-pyrrolo[2,3-d]pyrimidine]5'-[Rp/Sp-Methoxyalaninylphenylphosphate]

To a solution of the product of Example 1 (13 mg, 0.04 mmol) in THF (0.8 mL) were added methoxyalaninyl(phenyl)phosphorochloridate (35 mg, 0.12 mmol; prepared according to McGuigan et al. *J. Med. Chem.* 1993, 36, 1048-1052) and N-methylimidazole (20 mL, 0.24 mmol) with vigorous stirring. After 12 h of vigorous stirring at room temperature the solvent was removed under vacuum. The residue was dissolved in $CH_2Cl_2$ (10 mL) and washed with 1N aq. HCl (2×1.5 mL), sat. aq. $NaHCO_3$ (2×3 mL), water, sat. brine and dried ($MgSO_4$). The evaporated residue was purified on Phenomenex-$C_{18}$ reverse phase HPLC with a 0-99% B gradient over 35 min. at 10 mL/min (Solvent A=$H_2O$, Solvent B=MeCN). The target compound (Rp/Sp mixture) was isolated as a white solid in 3 mg (12%) yield.

$^1$HNMR($CD_3CN$): δ 8.20 (s, 1H), 7.51, 7.47 (2s, 1H), 7.39, 7.29, 7.21 (3m, 5H), 6.43, 6.44 (2d, 1H, $J_{H-F}$=19.1 and 18.8 Hz), 5.97 (br, 2H), 4.57-3.83 (m, 6H), 3.66, 3.64 (2s, 3H), 3.60, 3.66 (2s, 1H), 1.35, 1.30 (2d, 3H, J=7.0 Hz), 1.07, 1.04 (2d, 3H, $J_{H-F}$=22.9 Hz). $^{19}$F NMR ($CD_3CN$): δ −161.62, −161.89 (2br) $^{31}$P NMR ($CDCl_3$): δ 5.45, 4.75 MS: m/z 548 (M+1)

Example 7

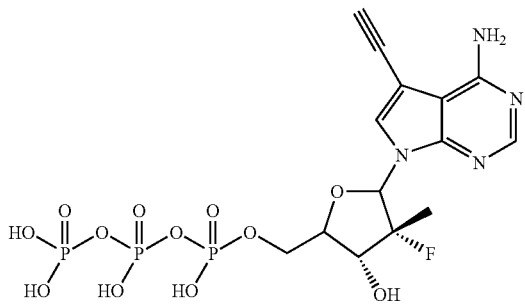

[4-Amino-5-ethynyl-7-(2-deoxy-2-fluoro-2-C-methyl-β-D-ribofuanosyl)-7H-pyrrolo[2,3-d]pyrimidine]5'-triphosphate To a solution of dry nucleoside from Example 1 (8.6 mg, 0.028 mmol) in trimethyl phosphate (0.5 mL) under Ar were added 4 Å molecular sieves. The mixture was stirred overnight at room temperature and then cooled to 0° C. Phosphorus oxychloride (5.1 µL, 0.056 mmol) was added and the resulting mixture was stirred at 0° C. for 1 h. Then tributylamine (20 µL, 0.084 mmol), acetonitrile (50 µL), and tributylammonium pyrophosphate (53 mg, 0.11 mmol) were added and the mixture was stirred for an additional 45 min. at 0° C. The reaction was quenched by addition of TEAB buffer (1M, 0.5 mL) and diluted with water (4 mL). The mixture was purified by ion exchange HPLC and desalted by RP-HPLC.

$^{31}$P NMR (D$_2$O): δ −7.74 (m), −10.27 (d, J=19.6 Hz), −21.68 (apparent t, J=20.5 Hz $^{19}$F NMR (D$_2$O): δ −161.69 (m) MS: m/z 545 (M-1)

Example 8

[4-Amino-5-ethynyl-7-(2-deoxy-2-fluoro-2-C-methyl-β-D-ribofuanosyl)-7H-pyrrolo[2,3-d]pyrimidine]5'-L-valyl ester To 4-Amino-5-ethynyl-7-(2-deoxy-2-fluoro-2-C-methyl-β-D-ribofuanosyl)-7H-pyrrolo[2,3-d]pyrimidine (0.4 mmol) in DMF is added Boc-L-valine (0.6 mmol), DECI (0.6 mmol) and DMAP (0.6 mmol). The mixture is stirred at ambient temperature for 24 h. and diluted with water. The mixture of 3'- and 5'-derivatives is separated by reverse phase chromatography.

Example 9

[4-Amino-5-ethynyl-7-(2-deoxy-2-fluoro-2-C-methyl-β-D-ribofuanosyl)-7H-pyrrolo[2,3-d]pyrimidine]5'-[Bis(S-pivaloyl-2-thioethyl)phosphate]

N4-(4-Monomethoxytrityl)-4-Amino-5-ethynyl-7-(2-deoxy-2-fluoro-2-C-methyl-β-D-ribofuanosyl)-7H-pyrrolo[2,3-d]pyrimidine (1 mmol) is mixed with 1H-tetrazole (0.7 mmol) and dried over P$_2$O$_5$ in vacuo overnight. The mixture is suspended in anhydrous acetonitrile (13 ml), bis(S-pivaloyl-2-thioethyl)N,N'-diisopropylphosphoramidite (0.7 mmol prepared according to Prakash et al. *J. Med. Chem.* 2005, 48 (4), 1199-1210) is added and the reaction mixture is stirred at ambient temperature for 8 hours under inert atmosphere. Solvent is removed under reduced pressure. The residue is cooled to −40° C., and a solution of 3-chloroperbenzoic acid (1.4 mmol) is added in 10 ml of CH$_2$Cl$_2$. The solution is allowed to warm up to room temperature over 1 h. Aqueous sodium sulfite (10 wt %, 2 ml) is added to reduce the excess of 3-chloroperbenzoic acid. The organic phase is separated, diluted with CH$_2$Cl$_2$, washed with saturated Na$_2$CO$_3$, and evaporated to dryness. The residue obtained is purified by flash silica gel column chromatography and eluted with 5% methanol in CH$_2$Cl$_2$. The mixture of 5'- and 3'-phosphates is dissolved in acetic acid/MeOH/water, 3:6:1 and heated at 55° C. for 24 h. Solvent is removed and the residue purified by HPLC on a reverse phase column.

Example 10

[4-Amino-5-ethynyl-7-(2-deoxy-2-fluoro-2-C-methyl-β-D-ribofuanosyl)-7H-pyrrolo[2,3-d]pyrimidine]5'-[Bis(S-(3-methyl-butyryl)-2-thioethyl)phosphate]

Compound is synthesized as in example 9 using bis(S-(3-methyl-butyryl)-2-thioethyl)N,N'-diisopropylphosphoramidite as a reagent.

Example 11

[4-Amino-5-ethynyl-7-(2-deoxy-2-fluoro-2-C-methyl-β-D-ribofuanosyl)-7H-pyrrolo[2,3-d]pyrimidine]5'-[Ethoxyalaninyl-phenylphosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and phenyl-(methoxy-L-alaninyl)-phosphochloridate (McGuigan et al. *Bioorganic & Medicinal Chem.* (13) 2005, 3219-3227).

Example 12

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-phenylphosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and phenyl-(benzyloxy-L-alaninyl)-phosphochloridate (McGuigan et al. *Bioorganic & Medicinal Chem.* (13) 2005, 3219-3227).

Example 13

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(naphthalen-2-yl)phosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and naphtalen-2-yl-(benzyloxy-L-alaninyl)-phosphochloridate (Congiatu et al. *J. Med. Chem.*, 49, 2006, 452-455).

Example 14

[4-Amino-5-ethynyl-7-(2-deoxy-2-fluoro-2-C-methyl-β-D-ribofuanosyl)-7H-pyrrolo[2,3-dipyrimidine]5'-[Benzyloxyalaninyl-(naphthalen-1-yl)phosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and naphtalen-1-yl-(benzyloxy-L-alaninyl)-phosphochloridate (Congiatu et al. *J. Med. Chem.*, 49, 2006, 452-455).

Example 15

[4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninylphenylphosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and phenyl-(Methoxy-L-phenylalaninyl)-phosphochloridate (Gudmundsson et al. *Nucleosides, Nucleotides & Nucleic Acids*, 23, (12) 2004, 1929-1937).

Example 16

[4-Amino-5-ethynyl-7-(2-deoxy-2-fluoro-2-C-methyl-β-D-ribofuanosyl)-7H-pyrrolo[2,3-d]pyrimidine]5'-[Methoxy—α,α dimethylglycylphenylphosphate]

The title compound is synthesized as described in McGuigan et al. *Bioorganic & Medicinal Chem.* (13) 2005, 3219-3227, using [4-Amino-5-ethynyl-7-(2-deoxy-2-fluoro-2-C-methyl-β-D-ribofuanosyl)-7H-pyrrolo[2,3-d]pyrimidine] and phenyl-(methyl-2-amino-2-methylpropanoate) phosphochloridate (McGuigan et al. *Bioorganic & Medicinal Chem.* (13) 2005, 3219-3227).

Biological Examples

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. *J. of Vir.*, 73:1649-1654, 1999; Ishii et al., *Hepatology*, 29:1227-1235, 1999; Lohmann et al., *J. Bio. Chem.*, 274:10807-10815, 1999; and Yamashita et al., *J. of Bio. Chem.*, 273:15479-15486, 1998.

WO 97/12033, filed on Sep. 27, 1996, by Emory University, listing C. Hagedorn and A. Reinoldus as inventors, which claims priority to U.S. Provisional Patent Application. Ser. No. 60/004,383, filed on September 1995, described an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; *Antiviral Therapy* 1996:1 (Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) was used for screening of compounds for inhibiting HCV RNA dependent RNA polymerase. The ET cell line was stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They were all available through Life Technologies (Bethesda, Md.). The cells were plated at $0.5$-$1.0 \times 10^4$ cells/well in the 96 well plates and incubated for 24 hrs before adding test compound. The compounds were added to the cells to achieve a final concentration of 0.1 nM to 50 µm and a final DMSO concentration of 0.5%. Luciferase activity was measured 48-72 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication data was plotted relative to no compound control. Under the same condition, cytotoxicity of the compounds was determined using cell proliferation reagent, WST-1 (Roche, Germany). The compounds showing antiviral activities, but no significant cytotoxicities were chosen to determine $IC_{50}$ and $TC_{50}$. For these determinations, a 10 point, 2-fold serial dilution for each compound was used, which spans a concentration range of 1000 fold. $IC_{50}$ and $TC_{50}$ values were calculated by fitting % inhibition at each concentration to the following equation:

$$\% \text{ inhibition} = 100\%/[(IC50/[I])^b + 1]$$

where b is Hill's coefficient.

The % inhibition at a particular concentration was determined using the following equation:

$$\% \text{ Inhibition} = 100 - [100*(Lum \text{ with inhibitor} - bg) / (Lum \text{ with no inhibitor} - bg)]$$

where bg was the background with no replicon cell, and Lum was the luminescence intensity of the reporter luciferase gene.

In this assay, 4-Amino-5-ethynyl-7-(2-deoxy-2-fluoro-2-C-methyl-β-D-ribofuanosyl)-7H-pyrrolo[2,3-d]pyrimidine exhibited 60% inhibition at 50 µM, and [4-Amino-5-ethynyl-7-(2-deoxy-2-fluoro-2-C-methyl-β-D-ribofuanosyl)-7H-pyrrolo[2,3-d]pyrimidine]5'-[Rp/Sp-Methoxyalaninylphenylphosphate] exhibited 11% inhibition at 12.5 µM.

Example 3

Cloning and Expression of Recombinant HCV-NS5b

The coding sequence of NS5b protein was cloned by PCR from pFKI$_{389}$luc/NS3-3'/ET as described by Lohmann, V., et al. (1999) *Science* 285, 110-113 using the primers shown on page 266 of WO 2005/012288.

The cloned fragment was missing the C terminus 21 amino acid residues. The cloned fragment was inserted into an IPTG-inducible expression plasmid that provides an epitope tag (His)6 at the carboxy terminus of the protein.

The recombinant enzyme was expressed in XL-1 cells and after induction of expression, the protein was purified using affinity chromatography on a nickel-NTA column. Storage condition was 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity was assayed by measuring incorporation of radiolabeled UTP into a RNA product using a biotinylated, heteropolymeric template, which includes a portion of the HCV genome. Typically, the assay mixture (34 µL) contains 10 mM Tris-HCl (pH 7.5), 5 mM MgCl$_2$, 0.2 mM EDTA, 10 mM KCl, 1 unit/µL RNAsin, 1 mM DTT, 10 µM each of NTP, including [$^3$H]-UTP, and 10 ng/µL biotinylated heteropolymeric template. 20× test compound in 2 µl's was then added as a 100% DMSO solution to achieve a final DMSO concentration of 5%. For IC50 determination a 10-point dose response was used. The compounds were serial diluted 2-fold thus covering a range of 1000 fold. Typically for IC50's, compounds were tested starting at 50 uM or 2 µM depending on the potency. Reactions were started with addition of 10× NS5B in 4 µl's and allowed to incubate at 37° C. for 2 hours. Reactions were quenched with 8 µL of 100 mM EDTA and reaction mixtures (30 µL) were transferred to streptavidin-coated scintillation proximity microtiter plates (FlashPlates) and incubated at 4° C. overnight. Incorporation of radioactivity was determined by scintillation counting (cpm). The % Inhibition at a particular concentration was determined using the following equation, $$\% \text{ Inhibition}=100-[100*(cpm \text{ with inhibitor}-bg)/(cpm \text{ with no inhibitor}-bg)]$$

where bg was the background with no enzyme.

In this assay, [4-Amino-5-ethynyl-7-(2-deoxy-2-fluoro-2-C-methyl-β-D-ribofuanosyl)-7H-pyrrolo[2,3-d]pyrimidine] 5'-triphosphate exhibited 95% inhibition at 6 µM.

Formulation Examples

The following are representative pharmaceutical formulations containing a compound of the present invention.

Example 1

Tablet Formulation

The following ingredients are mixed intimately and pressed into single scored tablets.

| Ingredient | Quantity per tablet, mg |
|---|---|
| Compound of the invention | 400 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
|---|---|
| Compound of the invention | 200 |
| Lactose, spray-dried | 148 |
| Magnesium stearate | 2 |

Example 3

Suspension Formulation

The following ingredients are mixed to form a suspension for oral administration.

| Ingredient | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Quantity per tablet, mg |
|---|---|
| Compound of the invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of the invention | 500 mg |
| Witepsol ® H-15 | balance |

What is claimed is:

1. A compound of formula I:

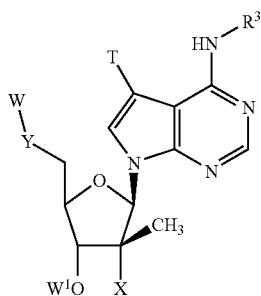

I wherein:

Y is O or $CH_2$;

X is selected from halo and $O-W^2$;

each of W, $W^1$ and $W^2$ is independently selected from the group consisting of hydrogen, $C_1$-$C_4$ alkyl, acyl, oxyacyl, phosphonate, phosphate esters, phosphate, phosphonamidate, phosphorodiamidate, phosphoramidate monoester, cyclic phosphoramidate, cyclic phosphorodiamidate, and phosphoramidate diester, provided that when X is $-O-W^2$, one of W, $W^1$ and $W^2$ is $C_1$-$C_4$ alkyl;

$R^3$ is selected from the group consisting of hydrogen, OH, acyl, $C_1$-$C_4$ alkyl, and $C_1$-$C_4$ alkoxy;

T is selected from the group consisting of:

a) $-C\equiv C-R$, where R is selected from the group consisting of:
  i) hydrogen;
  ii) tri($C_1$-$C_4$)alkylsilyl, $-C(O)NR^1R^2$, alkoxyalkyl, heteroaryl, substituted heteroaryl, phenyl, and substituted phenyl;
  where $R^1$ and $R^2$ are independently selected from the group consisting of hydrogen, alkyl, substituted alkyl, amino, substituted amino, aryl, substituted aryl, heteroaryl, substituted heteroaryl, heterocyclic and substituted heterocyclic provided that only one of $R^1$ and $R^2$ is amino or substituted amino, and further wherein $R^1$ and $R^2$, together with the nitrogen atom pendant thereto, form a heterocyclic or substituted heterocyclic; and
  iii) $-C(O)OR^{14}$, where $R^{14}$ is hydrogen, alkyl or substituted alkyl;

b) $-CH=CH-Q^2$, where $Q^2$ is selected from hydrogen or cis-alkoxy;

c) $-C(O)H$;

d) $-CH=NNHR^{15}$, where $R^{15}$ is hydrogen or $C_1$-$C_4$ alkyl;

e) $-CH=N(OR^{15})$, where $R^{15}$ is as defined above;

f) $-CH(OR^{16})_2$, where $R^{16}$ is $C_3$-$C_6$ alkyl;

g) $-B(OR^{15})_2$, where $R^{15}$ is as defined above; and h) $-NO_2$;

or pharmaceutically acceptable salts or partial salts thereof;

provided that when $R^3$ is hydrogen, OH, or $C_1$-$C_3$ alkoxy, then X is halo or $-O(C_1$-$C_4$ alkyl).

2. The compound according to claim 1, wherein X is halo.

3. The compound according to claim 2, wherein X is fluoro.

4. The compound according to claim 2, wherein T is $-C\equiv C-R$ and R is hydrogen.

5. The compound according to claim 2, wherein T is $-C\equiv C-R$ and R is selected from the group consisting of tri($C_1$-$C_4$)alkylsilyl, $-C(O)NR^1R^2$, alkoxyalkyl, heteroaryl, substituted heteroaryl, phenyl, and substituted phenyl.

6. The compound according to claim 5, wherein R is selected from the group consisting of phenyl, $-C(O)NH_2$, $-Si(CH_3)_3$, pyrid-2-yl, 4-methoxyphenyl, and $-CH(OCH_2CH_3)_2$.

7. The compound according to claim 2, wherein T is $-C\equiv C-R$ and R is $-C(O)OH$.

8. The compound according to claim 2, wherein T is $-C\equiv C-R$, R is $-C(O)OR^{14}$, and $R^{14}$ is alkyl.

9. The compound according to claim 2, wherein T is $-CH=CH-Q^2$, where $Q^2$ is selected from hydrogen or cis-methoxy.

10. The compound according to claim 2, wherein T is $-C(=O)H$.

11. The compound according to claim 2, wherein T is $-CH=NNHR^{15}$.

12. The compound according to claim 2, wherein T is $-CH=N(OR^{15})$.

13. The compound according to claim 2, wherein T is $-CH(OR^{16})_2$.

14. The compound according to claim 2, wherein T is $-B(OR^{15})_2$.

15. The compound according to claim 2, wherein T is $NO_2$.

16. The compound according to claim 2, wherein $R^3$ is hydrogen.

17. The compound according to claim 1, wherein X is $O-W^2$, and $W^2$ is $C_1$-$C_4$ alkyl.

18. The compound according to claim 17, wherein $W^2$ is methyl.

19. A compound of claim 1 having formula Ib:

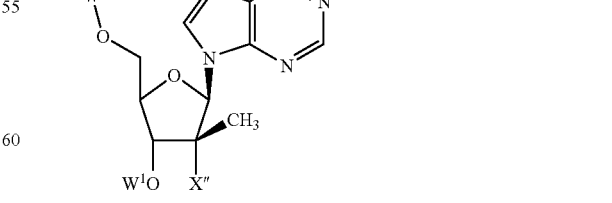

Ib wherein:

X" is halo;

each of W and $W^1$, is independently selected from the group consisting hydrogen of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^{30}$NHR$^{31}$ where R$^{30}$ is selected from the group consisting of hydrogen, alkyl, substituted alkyl, aryl, substituted aryl, heteroaryl and substituted heteroaryl and R$^{31}$ is hydrogen or R$^{30}$ together with the carbon atom pendent thereto and R$^{31}$ together with the nitrogen atom pendent thereto join to form a heterocyclic or substituted heterocyclic ring;

R$^3$ is selected from the group consisting of hydrogen, OH, acyl, $C_1$-$C_4$ alkyl, and $C_1$-$C_4$ alkoxy;

T is selected from the group consisting of:
a) —C≡C—R, where R is selected from the group consisting of
i) hydrogen;
ii) tri($C_1$-$C_4$)alkylsilyl, —C(O)NR$^1$R$^2$, alkoxyalkyl, heteroaryl, substituted heteroaryl, phenyl, and substituted phenyl;
where R$^1$ and R$^2$ are independently selected from the group consisting of hydrogen, alkyl, substituted alkyl, amino, substituted amino, aryl, substituted aryl, heteroaryl, substituted heteroaryl, heterocyclic and substituted heterocyclic provided that only one of R$^1$ and R$^2$ is amino or substituted amino, and further wherein R$^1$ and R$^2$, together with the nitrogen atom pendant thereto, form a heterocyclic or substituted heterocyclic;
iii) —C(O)OR$^{14}$, where R$^{14}$ is hydrogen, alkyl or substituted alkyl;
b) —CH=CH-Q$^2$, where Q$^2$ is selected from hydrogen or cis-alkoxy;
c) —C(O)H;
d) —CH=NNHR$^{15}$, where R$^{15}$ is hydrogen or $C_1$-$C_4$ alkyl;
e) —CH=N(OR$^{15}$), where R$^{15}$ is as defined above;
f) —CH(OR$^{16}$)$_2$, where R$^{16}$ is $C_3$-$C_6$ alkyl;
g) —B(OR$^{15}$)$_2$, where R$^{15}$ is as defined above; and
h) —NO$_2$;
or pharmaceutically acceptable salts thereof.

20. The compound according to claim 19 wherein X" is fluoro.

21. The compound according to claim 19, wherein T is —C≡C—R and R is hydrogen.

22. The compound according to claim 19, wherein T is —C≡C—R and R is selected from the group consisting of tri($C_1$-$C_4$)alkylsilyl, —C(O)NR$_1$R$^2$, alkoxyalkyl, heteroaryl, substituted heteroaryl, phenyl, and substituted phenyl.

23. The compound according to claim 22, wherein R is selected from the group consisting of phenyl, —C(O)NH$_2$, —Si(CH$_3$)$_3$, pyrid-2-yl, 4-methoxyphenyl, and —CH(OCH$_2$CH$_3$)$_2$.

24. The compound according to claim 19, wherein T is —C≡C—R and R is —C(O)OH.

25. The compound according to claim 19, wherein T is —C≡C—R, R is —C(O)OR$^{14}$, and R$^{14}$ is alkyl.

26. The compound according to claim 19, wherein T is —CH=CH-Q$^2$, where Q$^2$ is selected from hydrogen or cis-methoxy.

27. The compound according to claim 19, wherein T is —C(=O)H.

28. The compound according to claim 19, wherein T is —CH=NNHR$^{15}$.

29. The compound according to claim 19, wherein T is —CH=N(OR$^{15}$).

30. The compound according to claim 19, wherein T is —CH(OR$^{16}$)$_2$.

31. The compound according to claim 19, wherein T is —BC(OR$^{15}$)$_2$.

32. The compound according to claim 19, wherein T is NO$_2$.

33. The compound according to claim 19, wherein R$^{30}$, optionally together with R$^{31}$, is a sidechain of an amino acid.

34. The compound according to claim 33, wherein R$^{30}$, optionally together with R$^{31}$, is a sidechain of an L-amino acid.

35. The compound according to claim 19, wherein at least one of W or W$^1$ is hydrogen.

36. The compound according to claim 35, wherein both W and W$^1$ are hydrogen.

37. The compound according to claim 19, wherein one of W and W$^1$ is hydrogen, and the other of W and W$^1$ is represented by the formula:

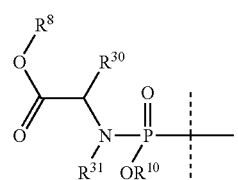

wherein R$^{31}$ is hydrogen, R$^{30}$ is a sidechain of an amino acid, or R$^{30}$ and R$^{31}$ together form the side chain of an amino acid, R$^8$ is hydrogen or alkyl, and R$^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic.

38. The compound according to claim 37 wherein R$^{30}$, optionally together with R$^{31}$, is a sidechain of an L-amino acid.

39. The compound according to claim 19, wherein one of W and W$^1$ is hydrogen, and the other of W and W$^1$ is represented by the formula:

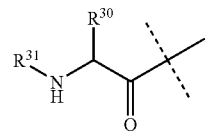

where R$^{31}$ is hydrogen and R$^{30}$, optionally together with R$^{31}$, is a side chain of an amino acid.

40. The compound according to claim 39, wherein R$^{30}$, optionally together with R$^{31}$, is a sidechain of an L-amino acid.

41. The compound according to claim 19, wherein R$^3$ is hydrogen.

42. The compound according to claim 1 selected from the group consisting of:
7-(2'-deoxy-2'-fluoro-2'-C-methyl-β-D-ribofuranosyl)-4-amino-5-nitro-pyrrolo[2,3-d]pyrimidine;
7-(2'-deoxy-2'-fluoro-2'-C-methyl-β-D-ribofuranosyl)-4-amino-5-(phenylacetylenyl)-pyrrolo[2,3-d]pyrimidine;
7-(2'-deoxy-2'-fluoro-2'-C-methyl-β-D-ribofuranosyl)-4-amino-5-formyl-pyrrolo[2,3-d]pyrimidine;
7-(2'-deoxy-2'-fluoro-2'-C-methyl-β-D-ribofuranosyl)-4-amino-5-boronic acid-pyrrolo[2,3-d]pyrimidine;

4-Amino-5-ethynyl-7-(2-deoxy-2-fluoro-2-C-methyl-β-D-ribofuanosyl)-7H-pyrrolo[2,3-d]pyrimidine;7-(2'-deoxy-2'-fluoro-2'-C-methyl-β-D-ribofuranosyl)-4-amino-5-(trimethylsilylacetylenyl)-pyrrolo[2,3-d]pyrimidine;

7-(2'-deoxy-2'-fluoro-2'-C-methyl-β-D-ribofuranosyl)-4-amino-5-ethenyl-pyrrolo[2,3-d]pyrimidine;

7-(2'-deoxy-2'-fluoro-2'-C-methyl-β-D-ribofuranosyl)-4-amino-5-methylenehydrazine-pyrrolo[2,3-d]pyrimidine;

7-(2'-deoxy-2'-fluoro-2'-C-methyl-β-D-ribofuranosyl)-4-amino-5-(carbaldehyde-oxime)-pyrrolo[2,3-d]pyrimidine;

7-(2'-deoxy-2'-fluoro-2'-C-methyl-β-D-ribofuranosyl)-4-hydroxyamino-5-nitro-pyrrolo[2,3-d]pyrimidine;

7-(2'-deoxy-2'-fluoro-2'-C-methyl-β-D-ribofuranosyl)-4-hydroxyamino-5-(phenylacetylenyl)-pyrrolo[2,3-d]pyrimidine;

7-(2'-deoxy-2'-fluoro-2'-C-methyl-β-D-ribofaranosyl)-4-hydroxyamino-5-formyl-pyrrolo[2,3-d]pyrimidine;

7-(2'-deoxy-2'-fluoro-2'-C-methyl-β-D-ribofuranosyl)-4-hydroxyamino-5-boronic acid-pyrrolo[2,3-d]pyrimidine;

7-(2'-deoxy-2'-fluoro-2'-C-methyl-β-D-ribofuranosyl)-4-hydroxyamino-5-acetylenyl-pyrrolo[2,3-d]pyrimidine;

7-(2'-deoxy-2'-fluoro-2'-C-methyl-β-D-ribofuranosyl)-4-hydroxyamino-5-(trimethylsilylacetylenyl)-pyrrolo[2,3-d]pyrimidine;

7-(2'-deoxy-2'-fluoro-2'-C-methyl-β-D-ribofuranosyl)-4-hydroxyamino-5-ethenyl-pyrrolo[2,3-d]pyrimidine;

7-(2'-deoxy-2'-fluoro-2'-C-methyl-β-D-ribofuranosyl)-4-hydroxyamino-5-methylenehydrazine-pyrrolo[2,3-d]pyrimidine;

7-(2'-deoxy-2'-fluoro-2'-C-methyl-β-D-ribofuranosyl)-4-hydroxyamino-5-(carbaldehyde-oxime)-pyrrolo[2,3-d]pyrimidine;

7-(2'-deoxy-2'-fluoro-2'-C-methyl-β-D-ribofuranosyl)-4-acetylamino-5-nitro-pyrrolo[2,3-d]pyrimidine;

7-(2'-deoxy-2'-fluoro-2'-C-methyl-β-D-ribofuranosyl)-4-acetylamino-5-(phenylacetylenyl)-pyrrolo[2,3-d]pyrimidine;

7-(2'-deoxy-2'-fluoro-2'-C-methyl-β-D-ribofuranosyl)-4-acetylamino-5-formyl-pyrrolo[2,3-d]pyrimidine;

7-(2'-deoxy-2'-fluoro-2'-C-methyl-β-D-ribofuranosyl)-4-acetylamino-5-boronic acid-pyrrolo[2,3-d]pyrimidine;

7-(2'-deoxy-2'-fluoro-2'-C-methyl-β-D-ribofuranosyl)-4-acetylamino-5-acetylenyl-pyrrolo[2,3-d]pyrimidine;

7-(2'-deoxy-2'-fluoro-2'-C-methyl-β-D-ribofuranosyl)-4-acetylamino-5-(trimethylsilylacetylenyl)-pyrrolo[2,3-d]pyrimidine;

7-(2'-deoxy-2'-fluoro-2'-C-methyl-β-D-ribofuranosyl)-4-acetylamino-5-ethenyl-pyrrolo[2,3-d]pyrimidine;

7-(2'-deoxy-2'-fluoro-2'-C-methyl-β-D-ribofuranosyl)-4-acetylamino-5-methylenehydrazine-pyrrolo[2,3-d]pyrimidine;

7-(2'-deoxy-2'-fluoro-2'-C-methyl-β-D-ribofuranosyl)-4-acetylamino-5-(carbaldehyde-oxime)-pyrrolo[2,3-d]pyrimidine;

7-(2'-deoxy-2'-fluoro-2'-C-methyl-β-D-ribofuranosyl)-4-ethoxyamino-5-nitro-pyrrolo[2,3-d]pyrimidine;

7-(2'-deoxy-2'-fluoro-2'-C-methyl-β-D-ribofuranosyl)-4-ethoxyamino-5-(phenylacetylenyl)-pyrrolo[2,3-d]pyrimidine;

7-(2'-deoxy-2'-fluoro-2'-C-methyl-β-D-ribofuranosyl)-4-ethoxyamino-5-formyl-pyrrolo[2,3-d]pyrimidine;

7-(2'-deoxy-2'-fluoro-2'-C-methyl-β-D-ribofuranosyl)-4-ethoxyamino-5-boronic acid-pyrrolo[2,3-d]pyrimidine;

7-(2'-deoxy-2'-fluoro-2'-C-methyl-β-D-ribofuranosyl)-4-ethoxyamino-5-acetylenyl-pyrrolo[2,3-d]pyrimidine;

7-(2'-deoxy-2'-fluoro-2'-C-methyl-β-D-ribofuranosyl)-4-ethoxyamino-5-(trimethylsilylacetylenyl)-pyrrolo[2,3-d]pyrimidine;

7-(2'-deoxy-2'-fluoro-2'-C-methyl-β-D-ribofuranosyl)-4-ethoxyamino-5-ethenyl-pyrrolo[2,3-d]pyrimidine;

7-(2'-deoxy-2'-fluoro-2'-C-methyl-β-D-ribofuranosyl)-4-ethoxyamino-5-methylenehydrazine-pyrrolo[2,3-d]pyrimidine;

7-(2'-deoxy-2'-fluoro-2'-C-methyl-β-D-ribofuranosyl)-4-ethoxyamino-5-(carbaldehyde-oxime)-pyrrolo[2,3-d]pyrimidine;

7-(2'-deoxy-2'-chloro-2'-C-methyl-β-D-ribofuranosyl)-4-amino-5-nitro-pyrrolo[2,3-d]pyrimidine;

7-(2'-deoxy-2'-chloro-2'-C-methyl-β-D-ribofuranosyl)-4-amino-5-(phenylacetylenyl)-pyrrolo[2,3-d]pyrimidine;

7-(2'-deoxy-2'-chloro-2'-C-methyl-β-D-ribofuranosyl)-4-amino-5-formyl-pyrrolo[2,3-d]pyrimidine;

7-(2'-deoxy-2'-chloro-2'-C-methyl-β-D-ribofuranosyl)-4-amino-5-boronic acid-pyrrolo[2,3-d]pyrimidine;

7-(2'-deoxy-2'-chloro-2'-C-methyl-β-D-ribofuranosyl)-4-amino-5-acetylenyl-pyrrolo[2,3-d]pyrimidine;

7-(2'-deoxy-2'-chloro-2'-C-methyl-β-D-ribofuranosyl)-4-amino-5-(trimethylsilylacetylenyl)-pyrrolo[2,3-d]pyrimidine;

7-(2'-deoxy-2'-chloro-2'-C-methyl-β-D-ribofuranosyl)-4-amino-5-ethenyl-pyrrolo[2,3-d]pyrimidine;

7-(2'-deoxy-2'-chloro-2'-C-methyl-β-D-ribofuranosyl)-4-amino-5-methylenehydrazine-pyrrolo[2,3-d]pyrimidine;

7-(2'-deoxy-2'-chloro-2'-C-methyl-β-D-ribofuranosyl)-4-amino-5-(carbaldehyde-oxime)-pyrrolo[2,3-d]pyrimidine;

7-(2'-deoxy-2'-chloro-2'-C-methyl-β-D-ribofuranosyl)-4-hydroxyamino-5-nitro-pyrrolo[2,3-d]pyrimidine;

7-(2'-deoxy-2'-chloro-2'-C-methyl-β-D-ribofuranosyl)-4-hydroxyamino-5-(phenylacetylenyl)-pyrrolo[2,3-d]pyrimidine;

7-(2'-deoxy-2'-chloro-2'-C-methyl-β-D-ribofuranosyl)-4-hydroxyamino-5-formyl-pyrrolo[2,3-d]pyrimidine;

7-(2'-deoxy-2'-chloro-2'-C-methyl-β-D-ribofuranosyl)-4-hydroxyamino-5-boronic acid-pyrrolo[2,3-d]pyrimidine;

7-(2'-deoxy-2'-chloro-2'-C-methyl-β-D-ribofuranosyl)-4-hydroxyamino-5-acetylenyl-pyrrolo[2,3-d]pyrimidine;

7-(2'-deoxy-2'-chloro-2'-C-methyl-β-D-ribofuranosyl)-4-hydroxyamino-5-(trimethylsilylacetylenyl)-pyrrolo[2,3-d]pyrimidine;

7-(2'-deoxy-2'-chloro-2'-C-methyl-β-D-ribofuranosyl)-4-hydroxyamino-5-ethenyl-pyrrolo[2,3-d]pyrimidine;

7-(2'-deoxy-2'-chloro-2'-C-methyl-β-D-ribofuranosyl)-4-hydroxyamino-5-methylenehydrazine-pyrrolo[2,3-d]pyrimidine;

7-(2'-deoxy-2'-chloro-2'-C-methyl-β-D-ribofuranosyl)-4-hydroxyamino-5-(carbaldehyde-oxime)-pyrrolo[2,3-d]pyrimidine;

7-(2'-deoxy-2'-chloro-2'-C-methyl-β-D-ribofuranosyl)-4-acetylamino-5-nitro-pyrrolo[2,3-d]pyrimidine;

7-(2'-deoxy-2'-chloro-2'-C-methyl-β-D-ribofuranosyl)-4-acetylamino-5-(phenylacetylenyl)-pyrrolo[2,3-d]pyrimidine;

7-(2'-deoxy-2'-chloro-2'-C-methyl-β-D-ribofuranosyl)-4-acetylamino-5-formyl-pyrrolo[2,3-d]pyrimidine;

7-(2'-deoxy-2'-chloro-2'-C-methyl-β-D-ribofuranosyl)-4-acetylamino-5-boronic acid-pyrrolo[2,3-d]pyrimidine;

7-(2'-deoxy-2'-chloro-2'-C-methyl-β-D-ribofuranosyl)-4-acetylamino-5-acetylenyl-pyrrolo[2,3-d]pyrimidine;

7-(2'-deoxy-2'-chloro-2'-C-methyl-β-D-ribofuranosyl)-4-acetylamino-5-(trimethylsilylacetylenyl)-pyrrolo[2,3-d]pyrimidine;

7-(2'-deoxy-2'-chloro-2'-C-methyl-β-D-ribofuranosyl)-4-acetylamino-5-ethenyl-pyrrolo[2,3-d]pyrimidine;

7-(2'-deoxy-2'-chloro-2'-C-methyl-β-D-ribofuranosyl)-4-acetylamino-5-methylenehydrazine-pyrrolo[2,3-d]pyrimidine;

7-(2'-deoxy-2'-chloro-2'-C-methyl-β-D-ribofuranosyl)-4-acetylamino-5-(carbaldehyde-oxime)-pyrrolo[2,3-d]pyrimidine;

7-(2'-deoxy-2'-chloro-2'-C-methyl-β-D-ribofuranosyl)-4-ethoxyamino-5-nitro-pyrrolo[2,3-d]pyrimidine;

7-(2'-deoxy-2'-chloro-2'-C-methyl-β-D-ribofuranosyl)-4-ethoxyamino-5-(phenylacetylenyl)-pyrrolo[2,3-d]pyrimidine;

7-(2'-deoxy-2'-chloro-2'-C-methyl-β-D-ribofuranosyl)-4-ethoxyamino-5-formyl-pyrrolo[2,3-d]pyrimidine;

7-(2'-deoxy-2'-chloro-2'-C-methyl-β-D-ribofuranosyl)-4-ethoxyamino-5-boronic acid-pyrrolo[2,3-d]pyrimidine;

7-(2'-deoxy-2'-chloro-2'-C-methyl-β-D-ribofuranosyl)-4-ethoxyamino-5-acetylenyl-pyrrolo[2,3-d]pyrimidine;

7-(2'-deoxy-2'-chloro-2'-C-methyl-β-D-ribofuranosyl)-4-ethoxyamino-5-(trimethylsilylacetylenyl)-pyrrolo[2,3-d]pyrimidine;

7-(2'-deoxy-2'-chloro-2'-C-methyl-β-D-ribofuranosyl)-4-ethoxyamino-5-ethenyl-pyrrolo[2,3-d]pyrimidine;

7-(2'-deoxy-2'-chloro-2'-C-methyl-β-D-ribofuranosyl)-4-ethoxyamino-5-methylenehydrazine-pyrrolo[2,3-d]pyrimidine;

7-(2'-deoxy-2'-chloro-2'-C-methyl-β-D-ribofuranosyl)-4-ethoxyamino-5-(carbaldehyde-oxime)-pyrrolo[2,3-d]pyrimidine;

7-(2'-deoxy-2'-bromo-2'-C-methyl-β-D-ribofuranosyl)-4-amino-5-nitro-pyrrolo[2,3-d]pyrimidine;

7-(2'-deoxy-2'-bromo-2'-C-methyl-β-D-ribofuranosyl)-4-amino-5-(phenylacetylenyl)-pyrrolo[2,3-d]pyrimidine;

7-(2'-deoxy-2'-bromo-2'-C-methyl-β-D-ribofuranosyl)-4-amino-5-formyl-pyrrolo[2,3-d]pyrimidine;

7-(2'-deoxy-2'-bromo-2'-C-methyl-β-D-ribofuranosyl)-4-amino-5-boronic acid-pyrrolo[2,3-d]pyrimidine;

7-(2'-deoxy-2'-bromo-2'-C-methyl-β-D-ribofuranosyl)-4-amino-5-acetylenyl-pyrrolo[2,3-d]pyrimidine;

7-(2'-deoxy-2'-bromo-2'-C-methyl-β-D-ribofuranosyl)-4-amino-5-(trimethylsilylacetylenyl)-pyrrolo[2,3-d]pyrimidine;

7-(2'-deoxy-2'-bromo-2'-C-methyl-β-D-ribofuranosyl)-4-amino-5-ethenyl-pyrrolo[2,3-d]pyrimidine;

7-(2'-deoxy-2'-bromo-2'-C-methyl-β-D-ribofuranosyl)-4-amino-5-methylhydrazine-pyrrolo[2,3-d]pyrimidine;

7-(2'-deoxy-2'-bromo-2'-C-methyl-β-D-ribofuranosyl)-4-amino-5-(carbaldehyde-oxime)-pyrrolo[2,3-d]pyrimidine;

7-(2'-deoxy-2'-methoxy-2'-C-methyl-β-D-ribofuranosyl)-4-amino-5-nitro-pyrrolo[2,3-d]pyrimidine;

7-(2'-deoxy-2'-methoxy-2'-C-methyl-β-D-ribofuranosyl)-4-amino-5-(phenylacetylenyl)-pyrrolo[2,3-d]pyrimidine;

7-(2'-deoxy-2'-methoxy-2'-C-methyl-β-D-ribofuranosyl)-4-amino-5-formyl-pyrrolo[2,3-d]pyrimidine;

7-(2'-deoxy-2'-methoxy-2'-C-methyl-β-D-ribofuranosyl)-4-amino-5-boronic acid-pyrrolo[2,3-d]pyrimidine;

7-(2'-deoxy-2'-methoxy-2'-C-methyl-β-D-ribofuranosyl)-4-amino-5-acetylenyl-pyrrolo[2,3-d]pyrimidine;

7-(2'-deoxy-2'-methoxy-2'-C-methyl-β-D-ribofuranosyl)-4-amino-5-(trimethylsilylacetylenyl)-pyrrolo[2,3-d]pyrimidine;

7-(2'-deoxy-2'-methoxy-2'-C-methyl-β-D-ribofuranosyl)-4-amino-5-ethenyl-pyrrolo[2,3-d]pyrimidine;

7-(2'-deoxy-2'-methoxy-2'-C-methyl-β-D-ribofuranosyl)-4-amino-5-methylenehydrazine-pyrrolo[2,3-d]pyrimidine;

7-(2'-deoxy-2'-methoxyo-2'-C-methyl-β-D-ribofuranosyl)-4-amino-5-(carbaldehyde-oxime)-pyrrolo[2,3-d]pyrimidine;

7-(2'-deoxy-2'-methoxy-2'-C-methyl-β-D-ribofaranosyl)-4-hydroxyamino-5-nitro-pyrrolo[2,3-d]pyrimidine;

7-(2'-deoxy-2'-methoxy-2'-C-methyl-β-D-ribofuranosyl)-4-hydroxyamino-5-(phenylacetylenyl)-pyrrolo[2,3-d]pyrimidine;

7-(2'-deoxy-2'-methoxy-2'-C-methyl-β-D-ribofuranosyl)-4-hydroxyamino-5-formyl-pyrrolo[2,3-d]pyrimidine;

7-(2'-deoxy-2'-methoxy-2'-C-methyl-β-D-ribofuranosyl)-4-hydroxyamino-5-boronic acid-pyrrolo[2,3-d]pyrimidine;

7-(2'-deoxy-2'-methoxy-2'-C-methyl-β-D-ribofuranosyl)-4-hydroxyamino-5-acetylenyl-pyrrolo[2,3-d]pyrimidine;

7-(2'-deoxy-2'-methoxy-2'-C-methyl-β-D-ribofuranosyl)-4-hydroxyamino-5-(trimethylsilylacetylenyl)-pyrrolo[2,3-d]pyrimidine;

7-(2'-deoxy-2'-methoxy-2'-C-methyl-β-D-ribofuranosyl)-4-hydroxyamino-5-ethenyl-pyrrolo[2,3-d]pyrimidine;

7-(2'-deoxy-2'-methoxy-2'-C-methyl-β-D-ribofuranosyl)-4-hydroxyamino-5-methylenehydrazine-pyrrolo[2,3-d]pyrimidine;

7-(2'-deoxy-2'-methoxyo-2'-C-methyl-β-D-ribofuranosyl)-4-hydroxyamino-5-(carbaldehyde-oxime)-pyrrolo[2,3-d]pyrimidine;

7-(2'-deoxy-2'-methoxy-2'-C-methyl-β-D-ribofuranosyl)-4-acetylamino-5-nitro-pyrrolo[2,3-d]pyrimidine;

7-(2'-deoxy-2'-methoxy-2'-C-methyl-β-D-ribofuranosyl)-4-acetylamino-5-(phenylacetylenyl)-pyrrolo[2,3-d]pyrimidine;

7-(2'-deoxy-2'-methoxy-2'-C-methyl-β-D-ribofuranosyl)-4-acetylamino-5-formyl-pyrrolo[2,3-d]pyrimidine;

7-(2'-deoxy-2'-methoxy-2'-C-methyl-β-D-ribofuranosyl)-4-acetylamino-5-boronic acid-pyrrolo[2,3-d]pyrimidine;

7-(2'-deoxy-2'-methoxy-2'-C-methyl-β-D-ribofuranosyl)-4-acetylamino-5-acetylenyl-pyrrolo[2,3-d]pyrimidine;

7-(2'-deoxy-2'-methoxy-2'-C-methyl-β-D-ribofuranosyl)-4-acetylamino-5-(trimethylsilylacetylenyl)-pyrrolo[2,3-d]pyrimidine;

7-(2'-deoxy-2'-methoxy-2'-C-methyl-β-D-ribofuranosyl)-4-acetylamino-5-ethenyl-pyrrolo[2,3-d]pyrimidine;

7-(2'-deoxy-2'-methoxy-2'-C-methyl-β-D-ribofuranosyl)-4-acetylamino-5-methylenehydrazine-pyrrolo[2,3-d]pyrimidine;

7-(2'-deoxy-2'-methoxyo-2'-C-methyl-β-D-ribofuranosyl)-4-acetylamino-5-(carbaldehyde-oxime)-pyrrolo[2,3-d]pyrimidine;

7-(2'-deoxy-2'-methoxy-2'-C-methyl-β-D-ribofuranosyl)-4-ethoxyamino-5-nitro-pyrrolo[2,3-d]pyrimidine;

7-(2'-deoxy-2'-methoxy-2'-C-methyl-β-D-ribofuranosyl)-4-ethoxyamino-5-(phenylacetylenyl)-pyrrolo[2,3-d]pyrimidine;

7-(2'-deoxy-2'-methoxy-2'-C-methyl-β-D-ribofuranosyl)-4-ethoxyamino-5-formyl-pyrrolo[2,3-d]pyrimidine;

7-(2'-deoxy-2'-methoxy-2'-C-methyl-β-D-ribofuranosyl)-4-ethoxyamino-5-boronic acid-pyrrolo[2,3-d]pyrimidine;

7-(2'-deoxy-2'-methoxy-2'-C-methyl-β-D-ribofuranosyl)-4-ethoxyamino-5-acetylenyl-pyrrolo[2,3-d]pyrimidine;

7-(2'-deoxy-2'-methoxy-2'-C-methyl-β-D-ribofuranosyl)-4-ethoxyamino-5-(trimethylsilylacetylenyl)-pyrrolo[2,3-d]pyrimidine;

7-(2'-deoxy-2'-methoxy-2'-C-methyl-β-D-ribofuranosyl)-4-ethoxyamino-5-ethenyl-pyrrolo[2,3-d]pyrimidine;

7-(2'-deoxy-2'-methoxy-2'-C-methyl-β-D-ribofuranosyl)-4-ethoxyamino-5-methylenehydrazine-pyrrolo[2,3-d]pyrimidine;

7-(2'-deoxy-2'-methoxyo-2'-C-methyl-β-D-ribofuranosyl)-4-ethoxyamino-5-(carbaldehyde-oxime)-pyrrolo[2,3-d]pyrimidine;

[4-Amino-5-ethynyl-7-(2-deoxy-2-fluoro-2-C-methyl-β-D-ribofuanosyl)-7H-pyrrolo[2,3-d]pyrimidine]5'-triphosphate;

[4-Amino-5-ethynyl-7-(2-deoxy-2-fluoro-2-C-methyl-β-D-ribofuanosyl)-7H-pyrrolo[2,3-d]pyrimidine]5'-[Rp/Sp-Methoxyalaninylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-L-valyl ester;

[4-Amino-5-ethynyl-7-(2-deoxy-2-fluoro-2-C-methyl-β-D-ribofuanosyl)-7H-pyrrolo[2,3-d]pyrimidine]5'-[Bis(S-pivaloyl-2-thioethyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Bis(S-(3-methyl-butyryl)-2-thioethyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-methoxyphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-fluorophenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Ethoxyalaninylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-methylphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyalaninyl-(4-propylphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-phenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(naphthalen-2-yl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(naphthalen-1-yl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(4-chloro-naphthalen-1-yl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxyalaninyl-(4-methoxy-naphthalen-1-yl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-methoxyphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-fluorophenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyphenylalaninyl-(4-methylphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyvalinylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-methoxyphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-fluorophenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxyvalinyl-(4-methylphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy(dimethylglycyl)phenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Benzyloxy-dimethylglycinylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy-dimethylglycinyl(4-fluorophenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy-dimethylglycinyl(4-methoxyphenyl)phosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy-dimethylglycinylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy-prolinylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Bezyloxy-prolinylphenylphosphate];

[4-Amino-5-ethynyl-7-(2-deoxy-2-fluoro-2-C-methyl-β-D-ribofuanosyl)-7H-pyrrolo[2,3-d]pyrimidine]5'-[Methoxy-prolinyl(4-fluorophenyl)phenylphosphate]; and

[4-Amino-5-ethynyl-7-(2-deoxy-2-fluoro-2-C-methyl-β-D-ribofuanosyl)-7H-pyrrolo[2,3-d]pyrimidine]5'-[Methoxy-prolinyl(4-methoxyphenyl)phenylphosphate].

43. A pharmaceutical composition comprising a pharmaceutically acceptable diluent and a compound according to claim 1 or a mixture of two or more of such compounds.

44. A method for treating a viral infection in a mammal mediated at least in part by a virus in the Flaviviridae family of viruses which method comprises administering to a mammal that has been diagnosed with said viral infection a pharmaceutical composition according to claim 43.

45. The method according to claim 44, wherein said virus is hepatitis C virus.

46. The method according to claim 45 in combination with the administration of a therapeutically effective amount of one or more agents active against hepatitis C virus.

47. The method of claim 46 wherein said active agent against hepatitis C virus is an inhibitor of HCV proteases, HCV polymerase, HCV helicase, HCV NS4B protein, HCV entry, HCV assembly, HCV egress, HCV NS5A protein, or inosine 5'-monophosphate dehydrogenase.

48. The method of claim 47 wherein said agent active against hepatitis C virus is interferon-alpha or pegylated interferon-alpha alone or in combination with ribavirin or levovirin.

* * * * *

UNITED STATES PATENT AND TRADEMARK OFFICE
CERTIFICATE OF CORRECTION

PATENT NO. : 7,405,204 B2
APPLICATION NO. : 11/411434
DATED : July 29, 2008
INVENTOR(S) : Christopher D. Roberts et al.

It is certified that error appears in the above-identified patent and that said Letters Patent is hereby corrected as shown below:

Claim 19, at Column 118, Line 67, please replace "group consisting hydrogen of acyl, oxyacyl, phospho-" with -- group consisting of hydrogen, acyl, oxyacyl, phospho- --.

Claim 31, at Column 120, Line 4, please replace "BC(OR$^{15}$)$_2$" with -- B(OR$^{15}$)$_2$ --.

Claim 42, at Column 121, Line 19, please replace "7-(2'-deoxy-2'-fluoro-2'-C-methyl-β-D-ribofaranosyl)-4" with -- 7-(2'-deoxy-2'-fluoro-2'-C-methyl-β-D-ribofuranosyl)-4 --.

Claim 42, at Column 124, Line 12, please replace "7-(2'-deoxy-2'-methoxy-2'-C-methyl-β-D-ribofaranosyl)" with -- 7-(2'-deoxy-2'-methoxy-2'-C-methyl-β-D-ribofuranosyl) --.

Signed and Sealed this

Twenty-fourth Day of February, 2009

JOHN DOLL
*Acting Director of the United States Patent and Trademark Office*